US012673132B2

(12) United States Patent
Mikos et al.

(10) Patent No.: US 12,673,132 B2
(45) Date of Patent: Jul. 7, 2026

(54) EXTRUSION PRINTING OF BIOCOMPATIBLE SCAFFOLDS

(71) Applicant: William Marsh Rice University, Houston, TX (US)

(72) Inventors: Antonios Georgios Mikos, Houston, TX (US); Jason Liwei Guo, Houston, TX (US); Luis Antonio Diaz-Gomez, Oviedo (ES); Anthony John Melchiorri, Houston, TX (US); Maryam Eugenia Elizondo, Houston, TX (US); Gerry Lynn Koons, Houston, TX (US); Panayiotis Dimitrios Kontoyiannis, Bellaire, TX (US)

(73) Assignee: William Marsh Rice University, Houston, TX (US)

( * ) Notice: Subject to any disclaimer, the term of this patent is extended or adjusted under 35 U.S.C. 154(b) by 864 days.

(21) Appl. No.: 17/904,266

(22) PCT Filed: Feb. 2, 2021

(86) PCT No.: PCT/US2021/016227
§ 371 (c)(1),
(2) Date: Aug. 15, 2022

(87) PCT Pub. No.: WO2021/162893
PCT Pub. Date: Aug. 19, 2021

(65) Prior Publication Data
US 2023/0091323 A1    Mar. 23, 2023

Related U.S. Application Data

(60) Provisional application No. 63/013,420, filed on Apr. 21, 2020, provisional application No. 62/976,414, filed on Feb. 14, 2020.

(51) Int. Cl.
| | |
|---|---|
| *A61L 27/18* | (2006.01) |
| *A61L 27/12* | (2006.01) |
| *A61L 27/22* | (2006.01) |
| *A61L 27/38* | (2006.01) |
| *A61L 27/56* | (2006.01) |
| *B28B 1/00* | (2006.01) |
| *B33Y 10/00* | (2015.01) |
| *B33Y 70/00* | (2020.01) |
| *C04B 35/447* | (2006.01) |
| *C04B 35/626* | (2006.01) |
| *C04B 35/634* | (2006.01) |
| *C04B 35/64* | (2006.01) |

(52) U.S. Cl.
CPC .............. *A61L 27/18* (2013.01); *A61L 27/12* (2013.01); *A61L 27/22* (2013.01); *A61L 27/3834* (2013.01); *A61L 27/56* (2013.01); *B28B 1/001* (2013.01); *B33Y 10/00* (2014.12); *B33Y 70/00* (2014.12); *C04B 35/447* (2013.01); *C04B 35/6269* (2013.01); *C04B*
*35/6346* (2013.01); *C04B 35/64* (2013.01); *A61L 2430/10* (2013.01); *C04B 2235/447* (2013.01); *C04B 2235/5436* (2013.01); *C04B 2235/5445* (2013.01); *C04B 2235/5454* (2013.01); *C04B 2235/6026* (2013.01)

(58) Field of Classification Search
None
See application file for complete search history.

(56) References Cited

U.S. PATENT DOCUMENTS

| | | | |
|---|---|---|---|
| 8,071,007 B1 | 12/2011 | Teoh et al. | |
| 10,752,772 B1 * | 8/2020 | Kogot .................... | C08G 63/06 |
| 2003/0114936 A1 | 6/2003 | Sherwood et al. | |
| 2012/0045487 A1 | 2/2012 | Lahann et al. | |
| 2018/0296343 A1 | 10/2018 | Wei | |
| 2019/0359766 A1 | 11/2019 | Becker et al. | |
| 2020/0281724 A1 * | 9/2020 | Weber .................... | A61L 27/12 |

FOREIGN PATENT DOCUMENTS

| | | |
|---|---|---|
| CN | 107899078 A | 4/2018 |

OTHER PUBLICATIONS

Boren, B., et al., J. Am. Chem. Soc. 130: 8923 â 8930 (2008). (Year: 2008).*
Chen, T., et al., e-Polymers 15(1): 3 â 13 (2015). (Year: 2015).*

(Continued)

*Primary Examiner* — David J Blanchard
*Assistant Examiner* — Daniel F Coughlin
(74) *Attorney, Agent, or Firm* — Osha Bergman Watanabe & Burton LLP

(57) ABSTRACT

Compositions and methods for making biocompatible articles are provided. A method includes preparing a 3D printable mixture and depositing successive layers of the mixture in a predetermined pattern to form a porous biocompatible article. The predetermined pattern has a porosity suitable for a bone or cartilage scaffold. Associated 3D printable compositions and porous articles made from the described methods are also described. The preparing a 3D printable mixture can comprise conjugating an alkyne-terminated polymer to a peptide to form a peptide-containing composite, or providing a mixture that comprises a ceramic material and a binder, and wherein the 3D printable mixture comprises from 50 wt. % to 80 wt. % of the ceramic material.

27 Claims, 12 Drawing Sheets
Specification includes a Sequence Listing.

(56) References Cited

OTHER PUBLICATIONS

Guo, J., et al., J Biomed Mater Res. 108A: 684 â 693 (2019). (Year: 2019).*

Kang, H.-W., Nature Biotechnology 34(3): 312 â 319 (2016). (Year: 2016).*

International Search Report issued in corresponding International Application No. PCT/US2021/016227 dated Jul. 5, 2021 (8 pages).

Written Opinion issued in corresponding International Application No. PCT/US2021/016227 dated Jul. 5, 2021 (11 pages).

Badev, A. et al.; "Photopolymerization kinetics of a polyether acrylate in the presence of ceramic fillers used in stereolithography"; Journal of Photochemistry and Photobiology A: Chemistry; vol. 222; Issue. 1; 2011; p. 117-122.

"Camacho, P. et al.; ""3D Printing with Peptide-Polymer Conjugates for Single-Step Fabrication of Spatially Functionalized Scaffolds""; Biomaterials Science; vol. 7; Issue. 10; 2019; p. 4237-4247 (11 pages) DOI: 10.1039/C9BM00887J.".

"Diaz-Gomez, L. et al.; ""Multimaterial Segmented Fiber Printing for Gradient Tissue Engineering""; Tissue Engineering Part C: Methods; vol. 25; Issue. 1; 2019; p. 12-24 (13 pages) DOI: 10.1089/ten.tec.2018.0307".

Diptanshu et al.; "Vat photopolymerization 3D printing of ceramics: Effects of fine powder"; Manufacturing Letters; vol. 21; 2019; pp. 20-23.

Du, Xiayou., Fu, S., and Zhu, Y.; "3D printing of ceramic-based scaffolds for bone tissue engineering: an overview"; Journal of Materials Chemistry B; vol. 6; Issue. 27; 2018; 4397.

Guo, J. L. et al.; "Modular, Tissue-Specific, and Biodegradable Hydrogel Cross-Linkers for Tissue Engineering"; Science Advances; vol. 5; Issue. 6; 2019; eaaw7396.

"Hanßke, F. et al.; ""Via Precise Interface Engineering towards Bioinspired Composites with Improved 3D Printing Processability and Mechanical Properties""; Journal of Materials Chemistry B; vol. 5; Issue. 25; 2017; p. 5037-5047 (11 pages) DOI: 10.1039/C7TB00165G.".

International Preliminary Report on Patentability issued in corresponding PCT Application No. PCT/US2021/016227, mailed on Aug. 11, 2022 (12 pages).

"Kumar, A. et al.; ""Three-dimensional plotted hydroxyapatite scaffolds with predefined architecture: comparison of stabilization by alginate cross-linking versus sintering""; Journal of Biomaterials Applications; vol. 30; issue. 8; 2016; 1168 DOI: 10.1177/0885328215617058".

Trachtenberg, Jordan E. et al.; "Extrusion-Based 3D Printing of Poly(Propylene Fumarate) Scaffolds With Hydroxyapatite Gradients"; Journal of Biomaterials Science, Polymer Edition; vol. 28; Issue. 6; 2017; p. 532-554 (23 pages).

* cited by examiner

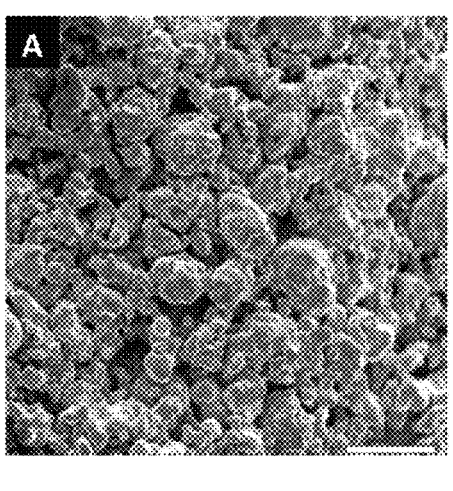
FIG. 9A
FIG. 9B
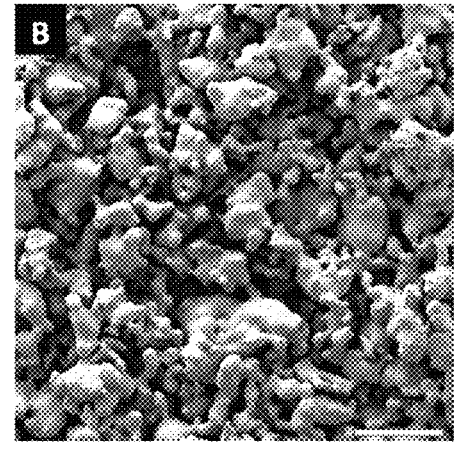
FIG. 10A
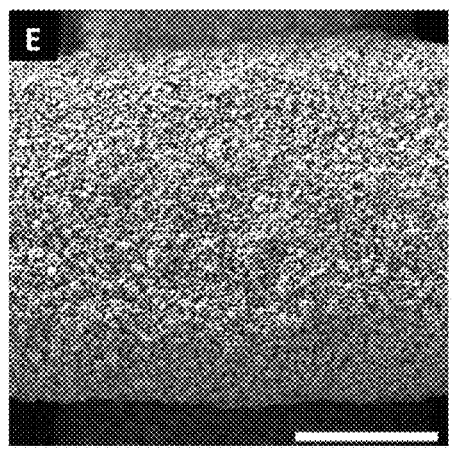
FIG. 10B
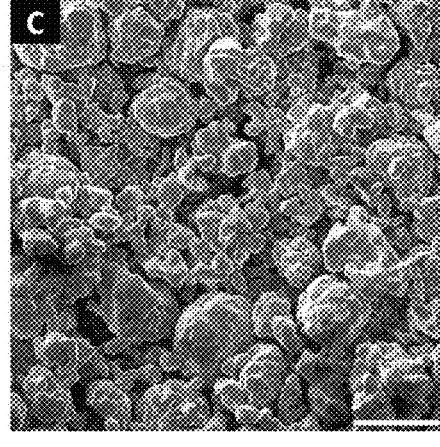
FIG. 11A
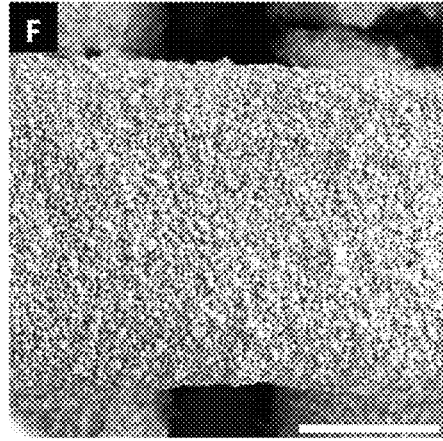
FIG. 11B

EXTRUSION PRINTING OF BIOCOMPATIBLE SCAFFOLDS

CROSS REFERENCE TO RELATED APPLICATIONS

This Application claims priority from Application 63/013,420 filed on Apr. 21, 2020 in the United States. This Application also claims priority from Application 62/976,414 filed on Feb. 14, 2020 in the United States. This Application also claims priority to International Application PCT/US2021/016227, filed on Feb. 2, 2021. Application 63/013,420, Application 62/976,414, and Application PCT/US2021/016227 are hereby incorporated by reference in their entireties.

STATEMENT REGARDING FEDERALLY SPONSORED RESEARCH OR DEVELOPMENT

This invention was made with Government Support under Grant Numbers P41-EB023833 and R01-AR068073 awarded by the National Institutes of Health. The government has certain rights in this invention.

BACKGROUND

The osteochondral unit is uniquely heterogeneous, consisting of a mineralized and highly vascularized subchondral bone layer, an acellular and avascular articular cartilage layer, and a gradient of tissue layers with biochemical and physical properties between those of bone and cartilage. Successful repair of osteochondral defects thus requires the replacement or regeneration of multiple tissue phenotypes, presenting significant clinical and scientific challenges in replicating the heterogenous properties of the osteochondral unit. Osteochondral repair remains a significant clinical challenge due to the multiple tissue phenotypes and complex biochemical milieu in the osteochondral unit. To repair osteochondral defects, it is necessary to mimic the gradation between bone and cartilage, which requires spatial patterning of multiple tissue-specific cues.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In one aspect, embodiments disclosed herein relate to a method of making a biocompatible article. The method may include preparing a 3D-printable mixture and depositing successive layers of the mixture in a predetermined pattern to form a porous biocompatible article. The predetermined pattern includes a porosity suitable for a bone or cartilage scaffold.

In another aspect, embodiments disclosed herein relate to a biocompatible 3D printable ink composition that includes a biocompatible ceramic material and a binder. The composition includes 50 wt. % to 80 wt. % of the ceramic material, which is selected from the group consisting of hydroxyapatite, alpha-tricalcium phosphate, beta-tricalcium phosphate, and combinations thereof.

Other aspects and advantages of the claimed subject matter will be apparent from the following description and the appended claims.

BRIEF DESCRIPTION OF DRAWINGS

FIGS. 9A and 9B are SEM micrographs of a sintered hydroxyapatite ceramic scaffold in accordance with one or more embodiments of the present disclosure.

FIGS. 10A and 10B are SEM micrographs of a sintered beta-tricalcium phosphate ceramic scaffold in accordance with one or more embodiments of the present disclosure.

FIGS. 11A and 11B are SEM micrographs of a sintered hydroxyapatite/beta-tricalcium phosphate ceramic scaffold in accordance with one or more embodiments of the present disclosure.

DETAILED DESCRIPTION

The present disclosure relates to methods of making biocompatible articles. Such articles may be useful for repair of bone and cartilage and in osteochondral units. In particular, the present disclosure relates to biocompatible articles containing tissue specific peptides and/or biocompatible ceramics. The compositions, methods and articles disclosed herein may be particularly useful in complex biological systems. Spatially patterned, tissue-specific scaffolds can be fabricated for the repair of complex, heterogeneous tissues including bone- and cartilage-like tissues.

In one aspect, a method of making a biocompatible article includes preparing a 3D-printable mixture and depositing successive layers of the mixture in a predetermined pattern to form a porous biocompatible article. The predetermined pattern includes a porosity suitable for a bone or cartilage scaffold.

In another aspect, methods of making a biocompatible article include preparing a first and a second 3D-printable mixtures and depositing successive layers of the mixtures in a predetermined pattern to form a porous biocompatible article. The predetermined pattern may provide for a structure having, for example, an interior patterned structure comprising the first 3D-printable mixture and an exterior patterned structure comprising the second 3D-printable mixture.

Figure 1:
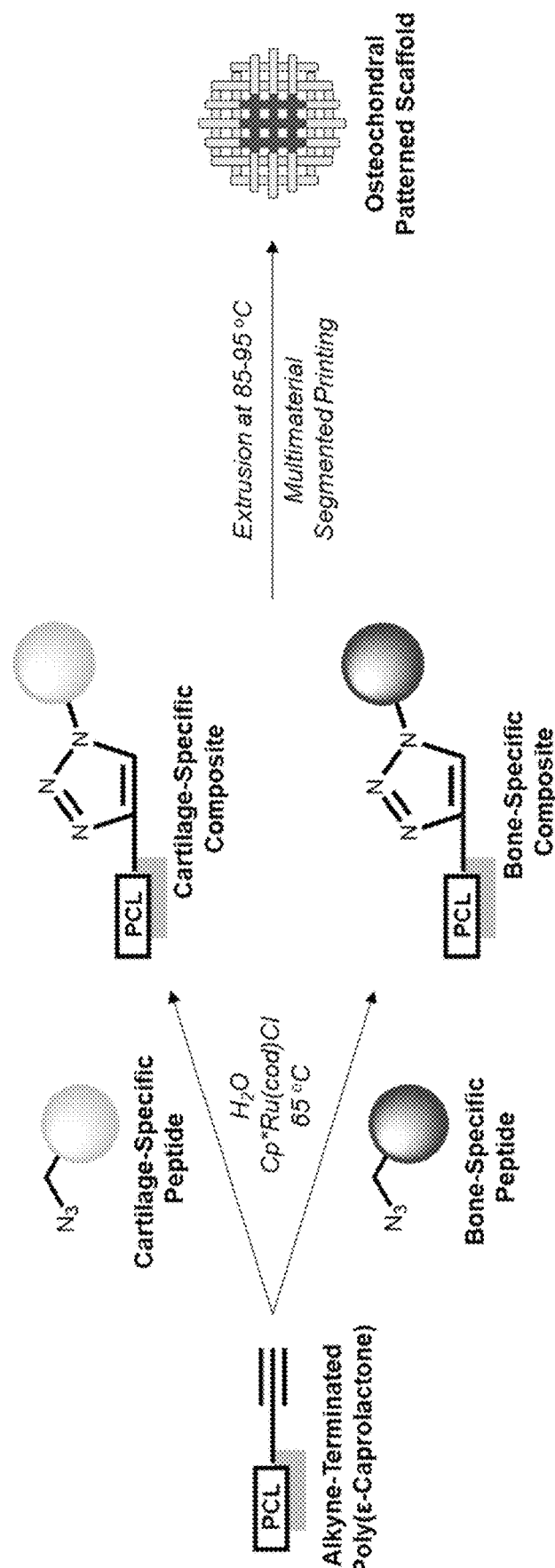
FIG. 1 is a schematic of a click conjugation and three-dimensional printing of composites in accordance with one or more embodiments of the present disclosure.

In some embodiments, the 3D printable mixture includes a peptide-containing composite. In such embodiments, the peptide-containing composite includes a peptide-conjugated polymer. The peptide-conjugated polymer may be prepared via a click conjugation reaction. The click conjugation reaction may include conjugating an alkyne-terminated polymer to a peptide to form a peptide-containing composite. The conjugation scheme may utilize a mild, aqueous, and chloro(pentamethylcyclopentadienyl)(cycloocta-diene) ruthenium(II) (Cp*Ru(cod)Cl) catalyzed alkyne-azide cycloaddition (RuAAC) that is bioorthogonal, non-cytotoxic, and compatible with biomolecules of diverse size and chemical character. The conjugating may include mixing the alkyne-terminated polymer, the peptide and a catalyst, for example Cp*Ru(cod)Cl, in an aqueous medium. The mixture may be held at a temperature of from 20 to 70° C. for a time of from 12 to 48 hours. A schematic of an exemplary click reaction with two exemplary peptides is shown in FIG. 1.

Any suitable alkyne-terminated polymer may be used for preparing a peptide-containing composite in accordance with one or more embodiments of the present disclosure. In some embodiments, the alkyne-terminated polymer is alkyne-terminated poly($\varepsilon$-caprolactone) (PCL). Alkyne-terminated poly($\varepsilon$-caprolactone) (PCL-alkyne) may be synthesized at molecular weights (MW) of 4-50 kDa by tin octoate-catalyzed ring opening polymerization at 150° C. with propargyl alcohol as an alkyne-presenting initiator, dissolved in dichloromethane, and precipitated in excess diethyl ether. The alkyne-terminated polymer may have a molecular weight having a lower limit of one of 4, 6, 8, 10, 15, 20, and 25 kDa and an upper limit of one of 35, 40, 45, and 50 kDa where any lower limit may be paired with any mathematically compatible upper limit.

Peptides suitable for specific tissue applications may be conjugated to the alkyne-terminated polymer. In one or more embodiments, the peptide is selected from the group consisting of an osteogenic bone morphogenetic protein mimetic peptide, an osteogenic glycine-histidine-lysine peptide, a chondrogenic N-cadherin peptide, and combinations thereof. To generate bone-specific composites, the osteogenic peptides bone morphogenetic protein mimetic peptide (BMPm, SEQ ID NO: 1) and glycine-histidine-lysine peptide (GHK, SEQ ID NO: 2), which have been implicated in the osteogenesis of osteoblasts and mesenchymal stem cells (MSCs) may be used. To generate cartilage-specific composites, N-cadherin peptide (NC, SEQ ID NO: 3), which mimics the N-cadherin protein that forms cell-cell contacts between MSCs during early chondrogenesis may be used. As may be appreciated by those skilled in the art, non-peptide biomolecules such as growth factors may also be suitable for conjugation by the methods described herein.

The click conjugation reactions described herein may utilize any suitable catalyst, for example, ruthenium- and copper-based catalysts. Examples of suitable catalysts include but are not limited to chloro(pentamethylcyclopentadienyl)(cycloocta-diene)ruthenium(II) (Cp*Ru(cod)Cl), $RuH_2(CO)(PPh_3)_3$), and $CuSO_4$.

Once the peptide-containing composite has been synthesized via the previously described click reaction, the peptide-containing composite may be extruded to form a 3D peptide-containing article. The peptide-containing composite may be extruded at a temperature of from 70 to 100° C., for example. The temperature of extrusion may have a lower limit of one of 70, 74, 76, 80, 82, and 85, ° C. and an upper limit of one of 87, 90, 92, 95, 97, and 100° C. where any lower limit may be paired with any mathematically compatible upper limit. In some embodiments, the peptide-containing composite may be extruded in a first direction with a space between each fiber of deposited composite. The article may then be rotated 90 degrees after a predetermined number of layers have been deposited. In some embodiments, article may then be rotated 90 degrees after the deposition of each successive layer. In some embodiments, the article may be rotated 90 degrees after the deposition of two or more layers having the same orientation. The resulting pattern forms a porous article with desired proportions and porosity.

Once deposited, the peptide-containing article may have a morphology and porosity suitable for biological applications, such as a bone or cartilage scaffold. As described herein, "porosity" means void space in the volume of the article. Unless otherwise indicated, the porosity described herein refers to macroporosity in the article, meaning porosity from macropores. Macropores are pores having a diameter of at least 20 μm and are generally pores formed in the spaces between printed fibers. As may be appreciated by those skilled in the art, printed fibers may include nano- and micro-scale pores within the fibers, however, such pores are not included in measurement of porosity described herein.

In one or more embodiments, the article may have fibers with a diameter of from 100 to 400 μm. The fiber diameter may have a lower limit of one of 100, 150, 200, 225, and 250 μm and an upper limit of one of 275, 300, 325, 350, 375 and 400 μm.

In one or more embodiments, the porosity of the peptide-containing article is from 60% to 85%. The porosity may have an upper limit of one of 75%, 80%, and 85% and a lower limit of one of 60%, 65% and 70%, where any upper limit may be combined with any mathematically compatible lower limit.

Peptide containing articles in accordance with some embodiments of the present disclosure may include pores having an average pore size suitable for biological applications. As used herein, "pore size" refers to the distance between two parallel printed fibers. The peptide-containing articles may have an average pore size of from 300 to 600 μm. The pore size may have a lower limit of one of 300, 325, 350, 375, 400, 425 and 450 μm, and an upper limit of one of 450, 475, 500, 525, 550 and 600 μm, where any lower limit may be combined with any mathematically compatible upper limit. As may be appreciated by those skilled in the art, the pore size, fiber size and porosity of the article may be adjusted to achieve particular morphologies.

Furthermore, heterogeneous materials may be spatially patterned to deposit multiple different materials in a single article. For example, multiple peptides may be printed in a single article in predetermined spatial arrangements, such as to result in a porous scaffold having an interior portion comprising a bone-specific composite and an exterior portion comprising a cartilage-specific composite. To demonstrate spatial patterning, PCL-peptide conjugates can be tagged with fluorescent dyes such as Pacific Blue (404/455 nm) and 5(6)-TAMRA (543/572 nm) by covalently attaching the dyes to lysine side chains on the peptide by stirring in THF at ambient temperature for 24 hours with catalysis by N,N-diisopropylethylamine. The product may be purified by precipitation in excess methanol. Fluorescently tagged PCL-peptides can be spatially patterned using the previously described extrusion methods and imaged by confocal microscopy.

Once a peptide-containing article has been fabricated, the bioactivity of the peptide-containing article may be determined via cell seeding the article. The articles may then be cultured in tissue-specific media to determine bioactivity.

As described above, embodiments of the present disclosure relate to a method of making a biocompatible article includes preparing a 3D-printable mixture and depositing successive layers of the mixture in a predetermined pattern to form a porous biocompatible article. In some embodiments, the 3D-printable mixture includes a ceramic material and a binder. The 3D printable mixture may include from 50 wt. % to 80 wt. % of the ceramic material. The ceramic material may have a lower limit of one of 50 wt. %, 55 wt. %, 60 wt. %, and 65 wt. %, and an upper limit of one of 70 wt. %, 75 wt. % and 80 wt. % based on the total amount of 3D printable mixture, where any lower limit may be paired with any mathematically compatible upper limit.

The 3D-printable mixture may include any suitable type of ceramic for use in biological systems. Calcium phosphates may be suitable due to their osteoconductive and osteoinductive properties. In particular embodiments, the ceramic material is selected from the group consisting of hydroxyapatite, alpha-tricalcium phosphate, beta-tricalcium phosphate, and combinations thereof.

The ceramic material may be in the form of a powder with a suitable particle size distribution for 3D printing. The ceramic powder may have an average particle size of from 50 nm to 50 μm. The average particle size may have a lower limit of one of 50, 100, 150, 200, 300, 400 and 500 nm and an upper limit of one of 1, 2, 5, 10, 20, 25, 35, 45 and 50 μm, where any lower limit may be used with any mathematically compatible upper limit.

As previously described, the 3D-printable mixture may include a binder. In some embodiments, the binder may be a photocurable resin, meaning the binder may crosslink upon exposure to UV radiation. In some embodiments, the binder includes tetrahydrofurfuryl methacrylate, urethane dimethacrylate, and diphenyl(2,4,6-trimethylbenzoyl)phosphine oxide. The tetrahydrofurfuryl methacrylate may be included in the 3D-printable mixture in an amount of 10 wt. % to 25 wt. % based on the total amount of 3D printable mixture. The urethane dimethacrylate may be included in the 3D-printable mixture in an amount of 5 wt. % to 10 wt. % based on the total amount of 3D printable mixture. The diphenyl(2,4,6-trimethylbenzoyl)phosphine oxide may be included in the 3D-printable mixture in an amount of 0.1 wt. % to 1.0 wt. % based on the total amount of 3D printable mixture.

The previously described ceramic material and binder may be mixed to form a slurry that may be used in 3D printing of biocompatible articles. The prepared slurry may advantageously be stable at room temperature for extended periods of time. Articles may be printed from a ceramic/binder slurry after 1, 2, 5, 7, 10, or 14 days of storage.

The 3D-printable mixture including a ceramic material and a binder may be extruded to form a biocompatible article. In some embodiments, extrusion may be performed at a temperature of from 10 to 40° C. and a pressure of from 0.3 to 8 bar. In some embodiments, the mixture may be extruded in a first direction with a space between each fiber of deposited mixture. After extrusion of a layer, ultraviolet radiation is applied to the layer. The article may be rotated by 90 degrees after a predetermined number of layers has been deposited. In some embodiments, the article may be rotated after each successive layer is deposited and cross-linked, and the process repeated until a ceramic article of the desired proportions is formed. In some embodiments, the article may be rotated by 90 degrees after two or more successive layers having the same orientation are deposited and crosslinked.

The porosity of the scaffolds herein may be achieved by depositing the ink fibers in layers with a patterned spacing within the layer. Alternating an orientation of consecutive layers may provide for the porosity. In some embodiments, consecutive layers may be deposited in the same orientation. The patterning, in some embodiments, may provide for complete interconnectivity of the pores of the scaffold.

Further, each layer of the scaffolds herein may be formed from one or more ceramics. In some embodiments, the scaffolds may be formed with distinct regional compositions, such as having a central portion having a first ceramic and a concentric ring surrounding the central portion having a second ceramic. Overlap of the ceramics may be provided for continuity of the layers.

An article deposited from a ceramic-containing mixture may optionally be heated to sinter the ceramic article. In some embodiments, the article may be sintered at a temperature of from 1000 to 1400° C. for 3 to 12 hours. Sintering conditions may be selected based upon the type of ceramic deposited and the ceramic content in the 3D printable mixture.

Articles deposited from a ceramic-containing mixture may have a morphology and porosity suitable for biological applications, such as a bone scaffold. Ceramic articles may have a fiber diameter from 300 to 850 μm. The fiber diameter may have a lower limit of one of 300, 350, 400, 450 and 500 μm and an upper limit of one of 550, 600, 650, 700, 750 and 800 μm, where any lower limit may be paired with any mathematically compatible upper limit.

Ceramic articles may have a porosity with a lower limit of one of 20%, 25%, 30%, and 35% and an upper limit of one of 40%, 45%, 50% and 55%, where any lower limit may be paired with any mathematically compatible upper limit.

Ceramic articles may have an average pore size with a lower limit of one of 600, 650, 700, and 750 μm and an upper limit of one of 800, 850, 900, 950 and 1000 μm, where any lower limit may be paired with any mathematically compatible upper limit. Ceramic articles may have pore sizes in a horizontal direction that are different from pore sizes in a vertical direction. As may be appreciated by those skilled in the art, the pore size, fiber size and porosity of the article may be adjusted to achieve particular morphologies.

The previously described compositions and methods may be used in combination to fabricate articles including peptides and ceramic materials. In some embodiments, a single construct may be fabricated to include a ceramic portion and a peptide-conjugated polymer portion. Such articles may be useful as tissue-specific components. Articles made from the methods disclosed herein may be used as vascularized grafts, a tendon implants and ligament implants, for example.

EXAMPLES

PCL-Peptide Articles
Materials

Fetal bovine serum (FBS) was purchased from Gemini Bio-Products (Sacramento, CA). Low glucose Dulbecco's modified eagle medium (DMEM), antibiotic-antimycotic, minimum essential medium alpha (α-MEM), Quant-iT PicoGreen dsDNA assay kit, and proteinase K were purchased from ThermoFisher Scientific (Waltham, MA). ITS+ Premix was purchased from Corning (Corning, NY). Phosphate buffered saline (PBS), ε-caprolactone, propargyl alcohol, Cp*Ru(cod)Cl, $CDCL_3$ with 1% (v/v) trimethylsilane, tetrahydrofuran (THF), N,N-diisopropylethylamine (DIEA), ascorbic acid, dexamethasone, β-glycerol 2-phosphate, acetic acid, pepstatin A, iodacetamide, tris(hydroxymethyl aminomethane), ethylenediaminetetraacetic acid (EDTA), 1,9-dimethyl-methylene blue (DMMB) zinc chloride double salt, and Costar Ultra-Low Attachment 24-well plates were purchased from MilliporeSigma (St. Louis, MO). 5-(and-6)-carboxytetramethylrhodamine, succinimidyl ester (TAMRA) dye was purchased from AAT Bioquest (Sunnyvale, CA). Pacific Blue dye was purchased from AdipoGen Life Sciences (San Diego, CA). Arsenazo III assay kit was purchased from Pointe Scientific (Canton, MI). Ultrapure water was obtained from a Millipore Super-Q water system (Billerica, MA).

Example 1: Synthesis of Tissue-Specific PCL Composites

The BMPm, (SEQ ID NO: 1, "GGGRHVRISRSL"), GHK (SEQ ID NO: 2, "GGGGHKSP"), and NC (SEQ ID NO: 3, "GGGHAVDI") peptide sequences with N-terminal azides were synthesized by solid phase peptide synthesis. Peptides are synthesized by 9-fluorenyl methoxycarbonyl (Fmoc) solid-phase peptide synthesis on a rink amide 4-methylbenzhydrylamine (MBHA) low-loading resin. To introduce N-terminal azides, 2-azidoacetic acid was added as the final "amino acid" by the same chemistry as regular amino acid addition. The peptide is cleaved from the resin using trifluoroacetic acid (TFA).

Alkyne-terminated PCL (PCL-alkyne) is available commercially, but in this case, was synthesized at a molar feed ratio of 200:1 ε-caprolactone:propargyl alcohol. Briefly, propargyl alcohol, ε-caprolactone, and stannous octoate are mixed under $N_2$ at 110° C. and stirred for 6 hours. The crude product is purified by dissolution in THF, followed by precipitation in excess methanol and vacuum filtration to collect the precipitate.

Bone- and cartilage-specific PCL-peptide composites were synthesized by the click conjugation of the azide-terminated peptides, BMPm (SEQ ID NO: 1), GHK (SEQ ID NO: 2), and NC (SEQ ID NO: 3), to PCL-alkyne. PCL-peptide composites were synthesized by mixing PCL-alkyne, the peptide of interest, and Cp*Ru(cod)Cl at 1:1:1 molar ratio in ultrapure $H_2O$ at 65° C. for 24 h, with stirring of the suspension by a mechanical stirrer at 400 rpm. After reaction, the aqueous portion was decanted to remove unreacted peptide and the majority of Cp*Ru(cod)Cl, after which the non-soluble product was dissolved in THF and precipitated in methanol to remove residual Cp*Ru(cod)Cl. The precipitated product was then collected by vacuum filtration. PCL-BMPm, PCL-GHK, and PCL-NC were synthesized with yields of 86.5%, 84.8%, and 85.7%, respectively.

Example 2: PCL Polymer Characterization $^1$H nuclear magnetic resonance spectroscopy (NMR) was used to measure the conversion of PCL-alkyne to PCL-peptide products using a 600 MHz Bruker spectrometer (Billerica, MA). Samples were dissolved in $CDCL_3$ with 1% (v/v) trimethylsilane, and spectra were processed using Bruker TopSpin software. Gel permeation chromatography (GPC) was used to characterize the molecular weight of PCL-alkyne and PCL-peptide composites before and after 3D printing. Samples were dissolved in THF and analyzed using a Waters Acquity Advanced Polymer Chromatography system (Milford, MA), with comparison to polystyrene standards of known molecular weight.

Figure 2A:
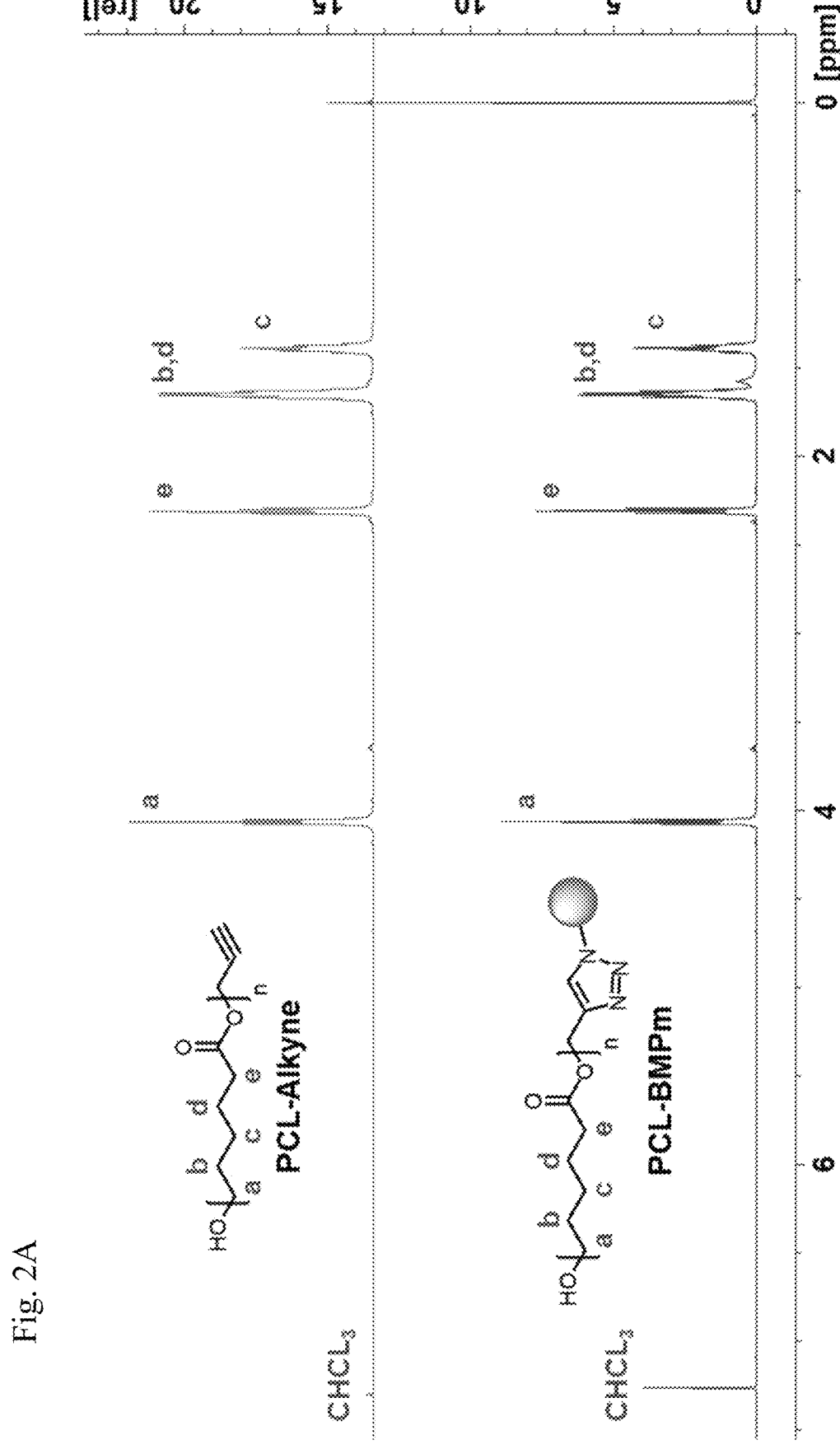
FIG. 2A is an NMR characterization of PCL-alkyne and PCL-peptide composites in accordance with one or more embodiments of the present disclosure.

Given that peptide conjugation represents the terminal modification of a large PCL-alkyne macromer (~22 kDa) with relatively smaller peptides (778-1380 Da), the bulk chemical structure (shown in the top trace of FIG. 2A) does not undergo any significant changes after modification with BMPm peptides (SEQ ID NO: 1; shown in the bottom trace of FIG. 2A). An area of interest from 4.6-5.2 ppm (as shown in FIG. 2B), however, can be used to assess reaction conversion.

Figure 2B:
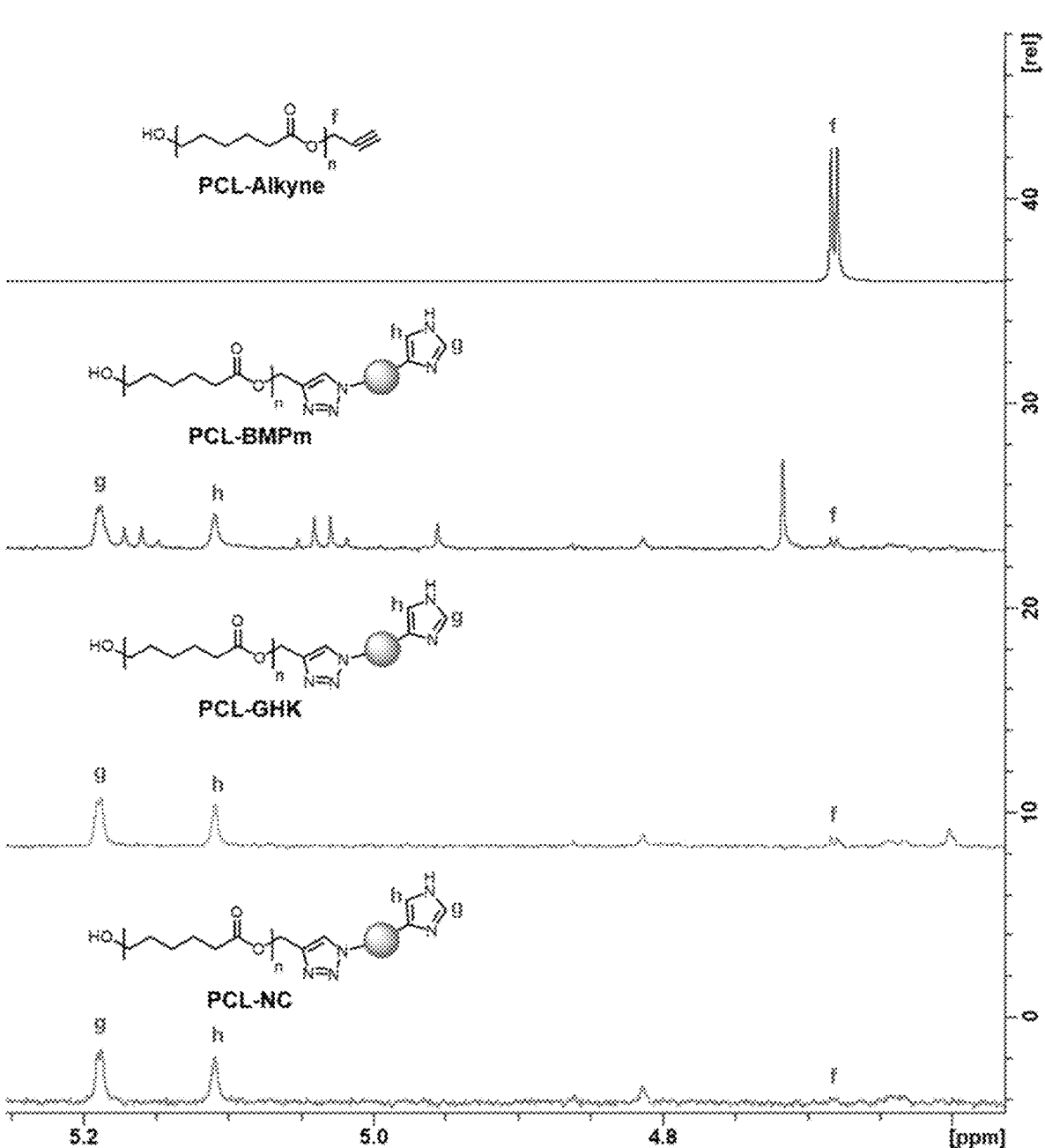
FIG. 2B is an expanded portion of the NMR characterization of PCL-alkyne and PCL-peptide composites shown in FIG. 2A.
Figures 3A, 3B, 3C, 3D:
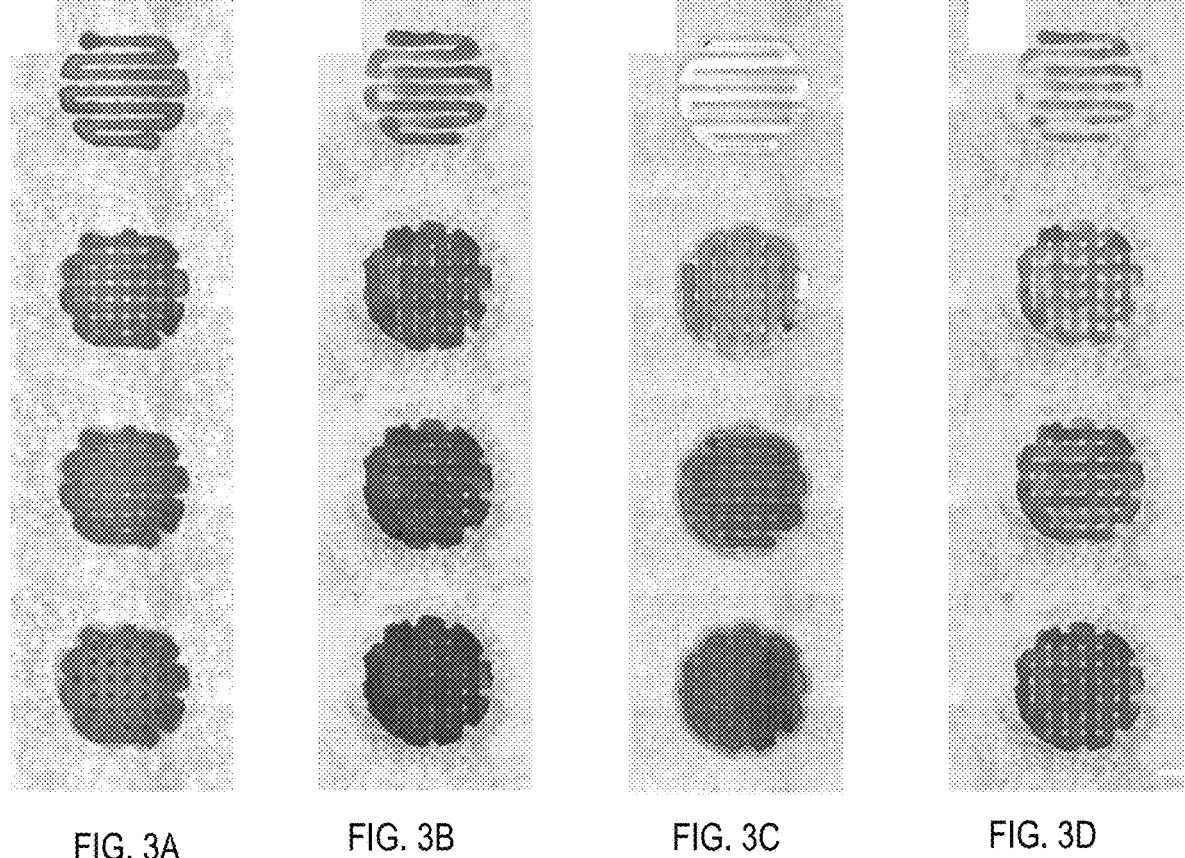
FIG. 3A is a photograph of layer-by-layer images of melt extruded PCL-alkyne in accordance with one or more embodiments of the present disclosure.
FIG. 3B is a photograph of layer-by-layer images of melt extruded PCL-BMPm in accordance with one or more embodiments of the present disclosure.
FIG. 3C is a photograph of layer-by-layer images of melt extruded PCL-GHK in accordance with one or more embodiments of the present disclosure.
FIG. 3D is a photograph of layer-by-layer images of melt extruded PCL-NC scaffolds in accordance with one or more embodiments of the present disclosure.

FIG. 2B shows this portion of the NMR spectra for, from top to bottom, PCL-alkyne, PCL-BMPm, PCL-GHK, and PCL-NC. The reaction can be assessed using both the disappearance of an alkyne-adjacent peak (marked "f") and the appearance of new peaks corresponding to the histidine side chain (marked "g" and "h"). For all PCL-peptide composites, the alkyne-adjacent peak disappeared after reaction, indicating quantitative conversion of the alkyne group. Furthermore, peaks corresponding to the histidine side chain were observable on all PCL-peptide spectra. Since free BMPm (SEQ ID NO: 1), GHK (SEQ ID NO: 2), and NC (SEQ ID NO: 3) peptides are insoluble in the CDCL$_3$ solvent used for NMR, the appearance of histidine peaks indicates conjugation of the peptides to PCL.

GPC data of PCL materials before and after conjugation and a discussion of the results may be found below following the discussion of 3D printing.

Example 3: Fabrication and Physical Characterization of 3D Printed PCL Constructs The 3D printed PCL constructs were fabricated by melt extrusion with an EnvisionTEC 3D Bioplotter Manufacturer (Gladbeck, Germany). The polymer of interest was placed in a metal cartridge, heated to 85-95° C., and extruded through a 27G needle at 4.9-5.1 bar pressure, 4.0 mm/s deposition speed, and 0.4 s pre-flow and post-flow, with imaging after each layer. Constructs were printed as a cylindrical, alternating crosshatch pattern with 4 layers of 5 mm diameter and 220 μm thickness, producing scaffolds with total dimensions of 5 mm diameter and 0.88 mm height.

The porosity, average fiber diameter, and average pore diameter of each construct was assessed by microcomputed tomography (μCT) using a Bruker SkyScan 1272 (Billerica, MA). Scans were acquired at a voltage of 40 kV and a current of 250 μA, with a rotation step size of 0.4°, 8 μm/pixel, frame averaging of 6, and random movement of 10. Reconstruction, slicing, and analysis were performed in Bruker NRecon and CTAn software (Billerica, MA) and LabView (Austin, TX). For quantification of physical architectural properties, a proportional volume of interest was set at 75% scale of the x, v, and z axes, equally spaced from the scaffold edges.

After confirming the successful synthesis of PCL-peptide composites, each material was printed by melt extrusion in a cylindrical crosshatch pattern, generating scaffolds with total dimensions of 5 mm diameter and 0.8 mm height. The printed scaffolds are shown in FIGS. 3A-3D (PCL-alkyne, PCL-BMPm, PCL-GHK, and PCL-NC, respectively). The results of the PCT analysis are shown in Table 1.

TABLE 1

| Scaffold Material | Porosity (%) | Average Fiber Diameter (μm) | Average Pore Diameter (μm) |
|---|---|---|---|
| PCL-Alkyne | 70.4 ± 8.1 | 258 ± 46 | 422 ± 40 |
| PCL-BMPm | 70.7 ± 4.2 | 262 ± 48 | 419 ± 37 |
| PCL-GHK | 78.2 ± 5.5 | 228 ± 30 | 478 ± 34 |
| PCL-NC | 71.8 ± 3.7 | 200 ± 9 | 432 ± 31 |

As shown, there were no significant differences in porosity, average fiber diameter, or average pore diameter between different scaffold materials, indicating that constructs could be reproducibly printed under similar conditions.

GPC was used to assess changes in the molecular weight distribution before and after peptide conjugation to PCL-alkyne and also before and after printing the scaffolds. The results are shown in Table 2.

TABLE 2

| Scaffold Material | $M_n$ (kDa) Before Printing | $M_n$ (kDa) After Printing | PDI Before Printing | PDI After Printing |
|---|---|---|---|---|
| PCL-Alkyne | 22.3 ± 0.4 | 22.1 ± 0.3 | 1.33 ± 0.01 | 1.33 ± 0.01 |
| PCL-BMPm | 27.2 ± 0.5 | 27.9 ± 0.3 | 1.22 ± 0.01 | 1.22 ± 0.01 |
| PCL-GHK | 24.0 ± 0.5 | 23.7 ± 0.5 | 1.29 ± 0.01 | 1.28 ± 0.01 |
| PCL-NC | 24.6 ± 0.4 | 24.6 ± 0.5 | 1.26 ± 0.01 | 1.27 ± 0.01 |

There were statistically significant changes in number-average molecular weight ($M_n$) and polydispersity index (PDI) after the conjugation of BMPm (SEQ ID NO: 1), GHK (SEQ ID NO: 2), and NC (SEQ ID NO: 3)_to PCL-alkyne. No significant changes in $M_n$ or PDI occurred as a result of melt extrusion, and NMR spectra also had no observable changes to chemical structure (data not shown).

Example 4: PCL-Peptide Patterning and Imaging

For fluorescent visualization, BMPm and NC peptides were synthesized with an extra lysine group for dye attachment (SEQ ID NO: 4, "GGGRHVRISRSLK" and SEQ ID NO: 5, "GGGHAVDIK," respectively), followed by conjugation to PCL-alkyne as described above. The PCL-BMPm and PCL-NC composites were then covalently linked to activated esters of Pacific Blue (405/455 nm excitation/emission) and TAMRA (543/572 nm excitation/emission), respectively. Briefly, the PCL-peptide composite, dye, and DIEA were dissolved in 1:1:1 molar ratio in THF, added to a N$_2$ purged flask, and stirred for 24 h at room temperature in the dark. After reaction, the product was precipitated in methanol and collected by vacuum filtration.

To demonstrate patterning, Pacific Blue-tagged PCL-BMPm and TAMRA-tagged PCL-NC were printed within cylindrical scaffolds of 10 mm diameter and 0.88 mm height, with each layer containing a centered 5 mm×5 mm square of PCL-BMPm surrounded by PCL-NC on all sides. The fluorescent scaffolds were imaged at 10× using a Nikon A1-Rsi confocal microscope (Tokyo, Japan), with automated stitching to generate a single image of the whole scaffold.

Figures 4A, 4B:
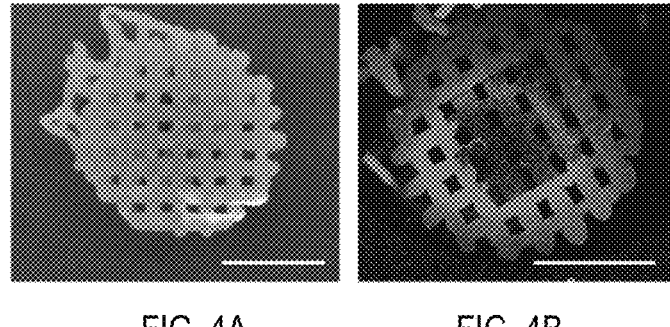
FIG. 4A is a photograph of a spatially patterned printed article in accordance with one or more embodiments of the present disclosure.
FIG. 4B is a fluorescent image of the printed article of FIG. 4A.

Heterogenous composite scaffolds were patterned with lateral patterning across horizontal layers and even individual fibers, as shown in FIGS. 4A and 4B. FIG. 4A is a photograph is a composite with fluorescently tagged PCL-BMPm and PCL-NC. FIG. 4B is a fluorescent imaging showing the distinction between PCL-BMPm (in the center) and PCL-NC (on the exterior) in the scaffold. The scale bars in FIGS. 4A and 4B are 5 millimeters.

Example 5: MSC Harvest and Culture

Rat bone marrow derived MSCs (mesenchymal stem cells) were harvested by aspiration of bone marrow from the tibia of five 6-8 week old male Fischer 344 rats from Charles River Laboratories (Wilmington, MA), in accordance with protocols approved by the Rice Institutional Animal Care and Use Committee and in agreement with the animal care and use guidelines set forth by the National Institutes of Health. Cells from all rats were pooled to minimize inter-animal variability. Adherent cells were cultured in growth medium (DMEM with 10% v/v FBS and 1% v/v antibiotic-antimycotic) inside a humidified incubator at 37° C. and 5% $CO_2$, and cryopreserved in liquid $N_2$ until point of usage. All MSCs were used at Passage 3.

Example 6: Cell Seeding and In Vitro Study Design

Printed constructs were sterilized by exposure of both sides to UV light for 3 h, immersion in a sterile gradient (100%, 75%, 50%, 25%, 0%) of ethanol and PBS, and two additional washes in PBS. MSCs were seeded on the scaffolds by pipetting 30 µL of a $3.3 \times 10^6$ cells/mL suspension on top of each scaffold in a low-attachment 24-well plate. After 2 h, 970 µL of growth medium was gently added to each well. After 24 h of cell attachment, the growth medium was replaced with either chondrogenic, osteogenic, or osteochondral medium.

Parallel chondrogenic (PCL-alkyne, PCL-NC) and osteogenic (PCL-alkyne, PCL-GHK) studies were conducted, in which scaffolds were cultured in both tissue-specific medium as well as mixed osteochondral medium. Chondrogenic medium contained DMEM supplemented with 1% v/v ITS+ Premix (6.25 µg/mL insulin, 6.25 µg/mL transferrin, 6.25 µg/mL selenous acid, 5.35 µg/mL linoleic acid and 1.25 µg/mL bovine serum albumin), 50 mg/L ascorbic acid, $10^{-7}$ M dexamethasone, and 1% v/v antibiotic-antimycotic, while osteogenic medium contained α-MEM supplemented with 10% v/v FBS, 50 mg/L ascorbic acid, $10^{-8}$ M dexamethasone, 10 mM β-glycerol 2-phosphate, and 1% v/v antibiotic-antimycotic. The mixed osteochondral medium consisted of a 1:1 mixture of the osteogenic and chondrogenic formulations. Scaffolds were cultured for up to 28 days, with replacement of medium every 2-3 days.

Example 7: Biochemical Assays

After 0, 7, 14, or 28 days of culture, scaffolds were digested and assayed for cellularity and tissue-specific ECM (extracellular matrix) deposition using the PicoGreen assay (DNA content), DMMB assay (cartilage-specific sulfated glycosaminoglycans), and Arsenazo III assay (bone-specific mineralization) 1121. Scaffolds were washed in PBS for 10 min at 37° C. and then transferred to sterile pre-weighed polystyrene tubes containing 5 mm stainless steel beads. After weighing, each scaffold was frozen at −20° C. until ready for characterization. Thawed samples were homogenized in 300 µL of proteinase K solution (PicoGreen, DMMB) or 300 µL of 0.5M acetic acid (Arsenazo III) using a Qiagen TissueLyser II (Hilden, Germany) at 30 s$^{-1}$ for 5 min. The proteinase K solution consisted of 1 mg/mL proteinase K, 10 µg/mL pepstatin A, and 185 µg/mL iodoacetamide in tris-EDTA solution (6.055 mg/mL tris(hydroxymethyl aminomethane), 0.372 mg/mL EDTA, pH 7.6). After homogenization, the proteinase K and acetic acid suspensions were allowed to digest for 16 h at 65° C. and room temperature, respectively, followed by quantification of biochemical content using assay kits. All biochemical data were normalized to acellular controls that were cultured under the same conditions.

The bioactivity of PCL-peptide composites was determined by seeding MSCs on 3D printed constructs and investigating their ability to promote bone- and cartilage-specific ECM deposition in vitro. The cellular activity data at 0, 7, 14 and 28 days is shown in FIGS. 5A-5E. The data in FIGS. 5A-5E are reported as means±standard deviation for a sample size of n=3. * indicates statistical significance compared to a peptide-free PCL-alkyne control in the same medium formulation and same timepoint. # indicates significance compared to the same scaffold material and medium formulation at Day 0.

Figure 5A:
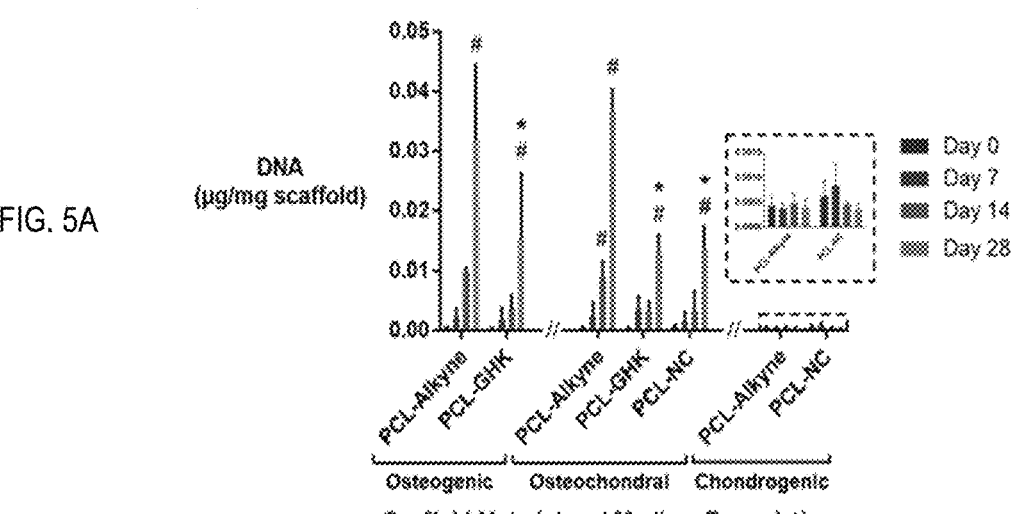
FIG. 5A is a graph of DNA content for various materials over time in accordance with one or more embodiments of the present disclosure.

The DNA content normalized to scaffold mass is shown in FIG. 5A. PCL-alkyne scaffolds showed a large amount of cell proliferation over time in osteogenic and osteochondral media, while PCL-GHK and PCL-NC scaffolds demonstrated statistically lower proliferation in both media. All scaffolds cultured in serum-free chondrogenic medium did not undergo cell proliferation and maintained static levels of DNA over 28 days of culture.

Figure 5B:
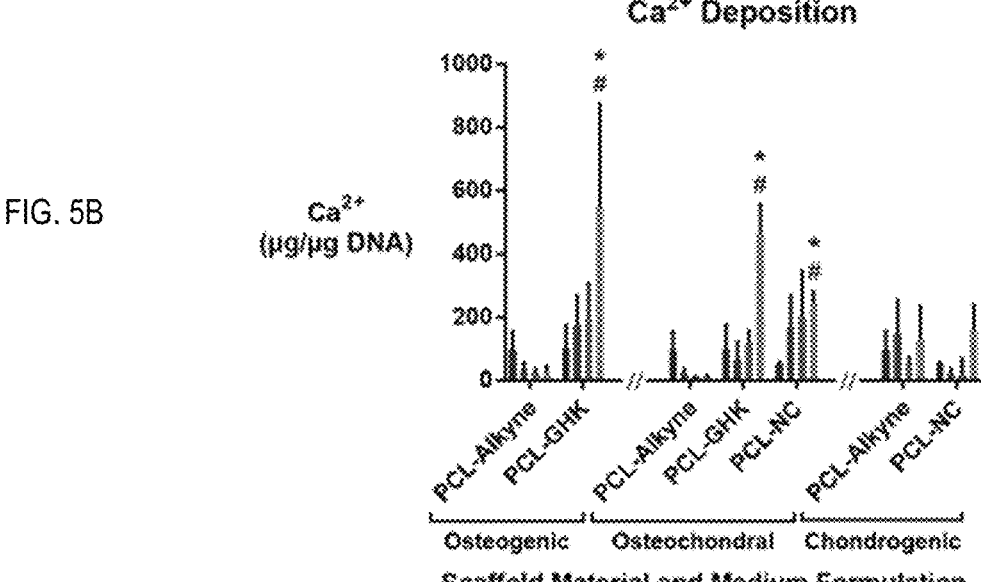
FIG. 5B is a graph of calcium content for various materials over time in accordance with one or more embodiments of the present disclosure.
Figure 5C:
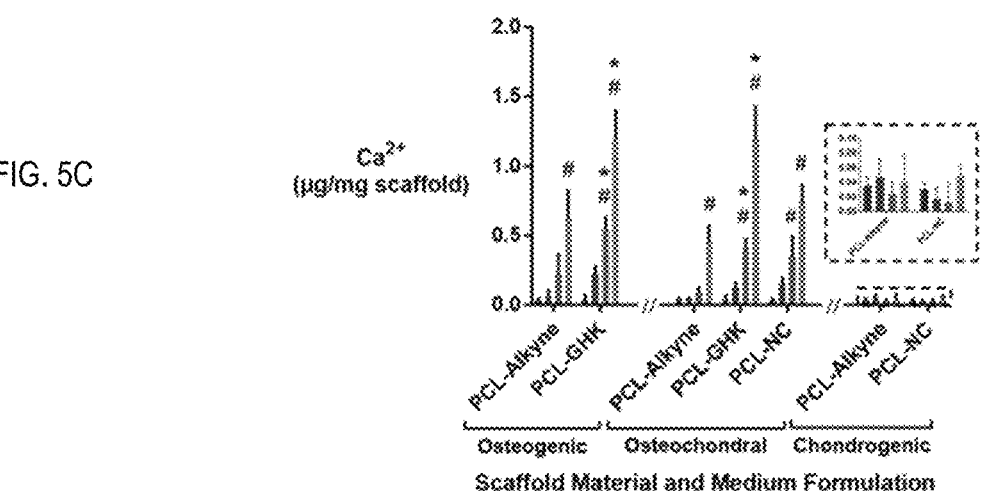
FIG. 5C is a graph of calcium content for various materials over time in accordance with one or more embodiments of the present disclosure.

Bone-specific calcium content normalized to cellular content is shown in FIG. 5B. Bone-specific calcium content normalized to scaffold mass is shown in FIG. 5C. PCL-GHK constructs promoted the greatest amount of bone-specific mineralization per cell in both osteogenic and mixed osteochondral media and also achieved the highest level of scaffold mineralization in both media. PCL-NC also promoted greater mineralization per cell in the mixed osteochondral medium but did not produce statistically significant effects on scaffold mineralization. No scaffolds cultured in chondrogenic medium underwent statistically significant mineralization when normalized to either cellular content or scaffold mass.

Figure 5D:
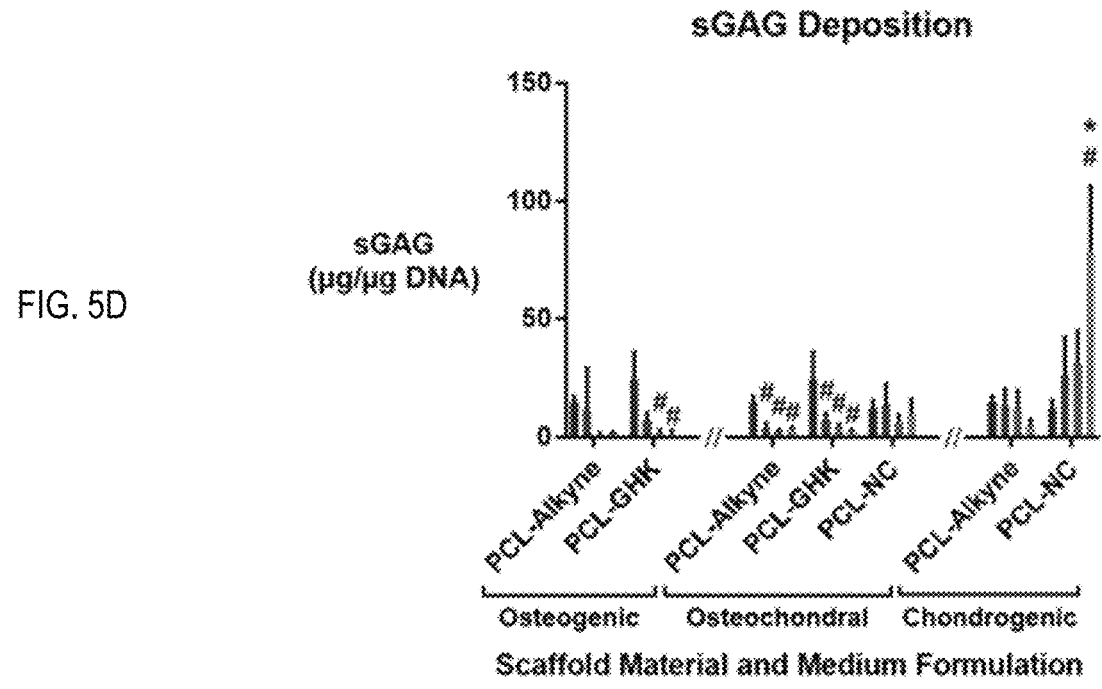
FIG. 5D is a graph of cartilage-specific sulfated glycosaminoglycan (sGAG) content over time in accordance with one or more embodiments of the present disclosure.
Figure 5E:
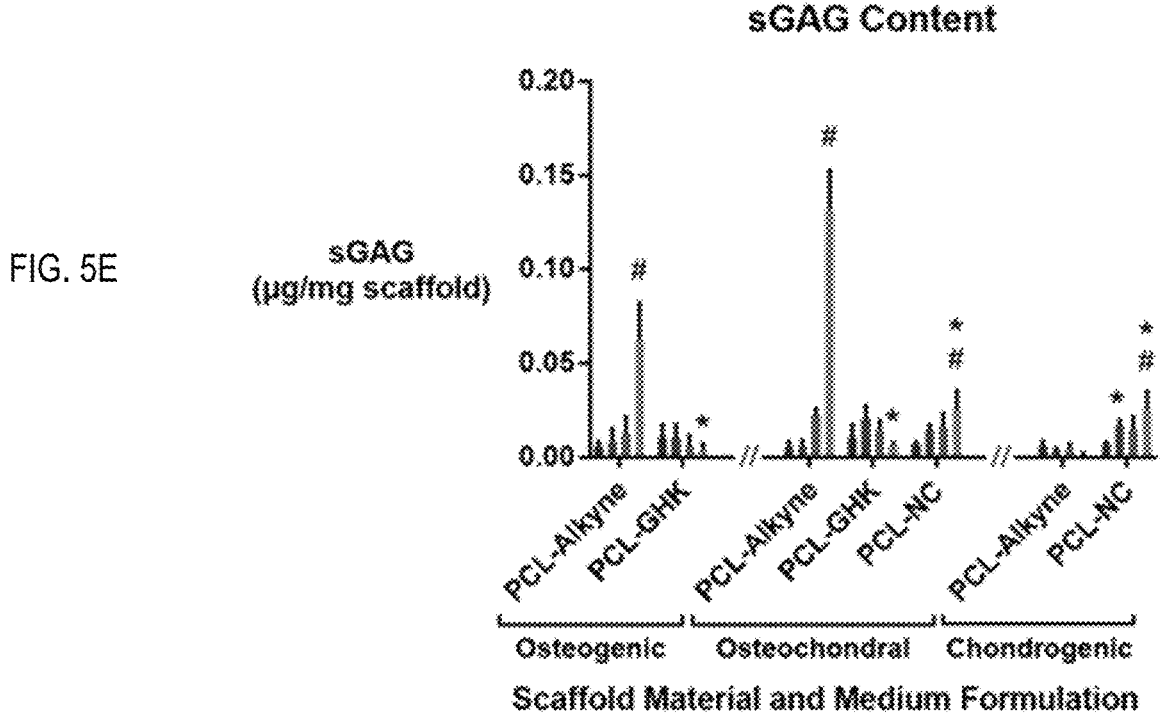
FIG. 5E is a graph of cartilage-specific sulfated glycosaminoglycan (sGAG) content over time in accordance with one or more embodiments of the present disclosure.

Cartilage-specific sulfated glycosaminoglycan (sGAG) content normalized to cellular content is shown in FIG. 5D. Cartilage-specific sulfated glycosaminoglycan (sGAG) content normalized to scaffold mass is shown in FIG. 5E. PCL-NC produced a large spike in cartilage-specific sGAG deposition per cell by day 28 in chondrogenic medium, whereas PCL-alkyne did not exhibit any changes in cell-normalized sGAG deposition over time. PCL-NC also maintained a constant level of sGAG deposition per cell in mixed osteochondral medium, in which PCL-alkyne and PCL-GHK both exhibited decreasing amounts of cell-normalized sGAG deposition over time. PCL-alkyne scaffolds had higher proportions of sGAG content by scaffold mass in both osteogenic and mixed osteochondral media as a result of cell proliferation in these media, but they did not experience significant changes in mass-normalized sGAG content when cultured in serum-free chondrogenic medium. PCL-NC, on the other hand, demonstrated a statistically significant increase in mass-normalized sGAG content when cultured in chondrogenic medium.

Ceramic Articles

Materials

Hydroxyapatite (HA; average diameter 25.1 µm) and sintered β-tricalcium phosphate (β-TCP; average diameter 5.3 µm) powders were obtained from Sigma-Aldrich (St. Louis, MO). E-Shell® 300, a methacrylate-based photocurable resin consisting of tetrahydrofurfuryl methacrylate (THFMA), urethane dimethacrylate (UDMA), and diphenyl (2,4,6-trimethylbenzoyl)phosphine oxide (TPO), was acquired from EnvisionTEC (Gladbeck, Germany). Unless otherwise indicated, all chemicals were used as received.

Example 7: Ceramic Ink Preparation

Printable inks were prepared by dispersing the ceramic powders in E-Shell® 300. To this end, HA, β-TCP or 50:50 w/w % β-TCP:HA (hereafter referred to as TCP/HA) powders were placed in a mortar. Thereafter, E-Shell® & 300 was added to the powder dropwise to obtain a 70:30 w/w % ratio of ceramic to E-Shell®300. The components were then mixed using a pestle until homogeneous slurry was formed.

Example 8: Ceramic Scaffold 3D Printing

The inks were then loaded in printing cartridges with a 20G needle (inner diameter: 0.60 mm). Cylindrical scaffold designs (diameter 10 mm; height 5 mm) were created in SketchUp (Trimble, Sunnyvale, CA) and sliced into 16 layers (0.32 mm slicing thickness) using BioplotterRP Software (EnvisionTEC, Gladbeck, Germany). A filling pattern was designated by drawing parallel straight continuous fibers with a 1.4 mm on-center spacing. Each two consecutive layers were designed to have the same orientation in order to form vertical pores for complete pore interconnectivity within the scaffold. The next two consecutive layers were then printed with the same pattern at a 90° rotated orientation.

Extrusion-based 3D printing was then performed using an EnvisionTEC 3D-Bioplotter (Gladbeck, Germany). All ceramic ink compositions were printed using a printing pressure of 1 bar, printing speed of 12 mm/s, and needle offset of 0.2 mm. After the extrusion of each layer, an ultraviolet (UV) head was used to cure the deposited ceramic ink for 10 s. The scaffolds used for morphological, structural, mechanical, and dissolution analyses were printed with the above-mentioned 3D model design with sixteen layers in total, while scaffolds used for the storability studies were also printed with eight layers in total.

Figures 6A, 6B, 6C, 7A, 7B, 7C, 8A, 8B, 8C:
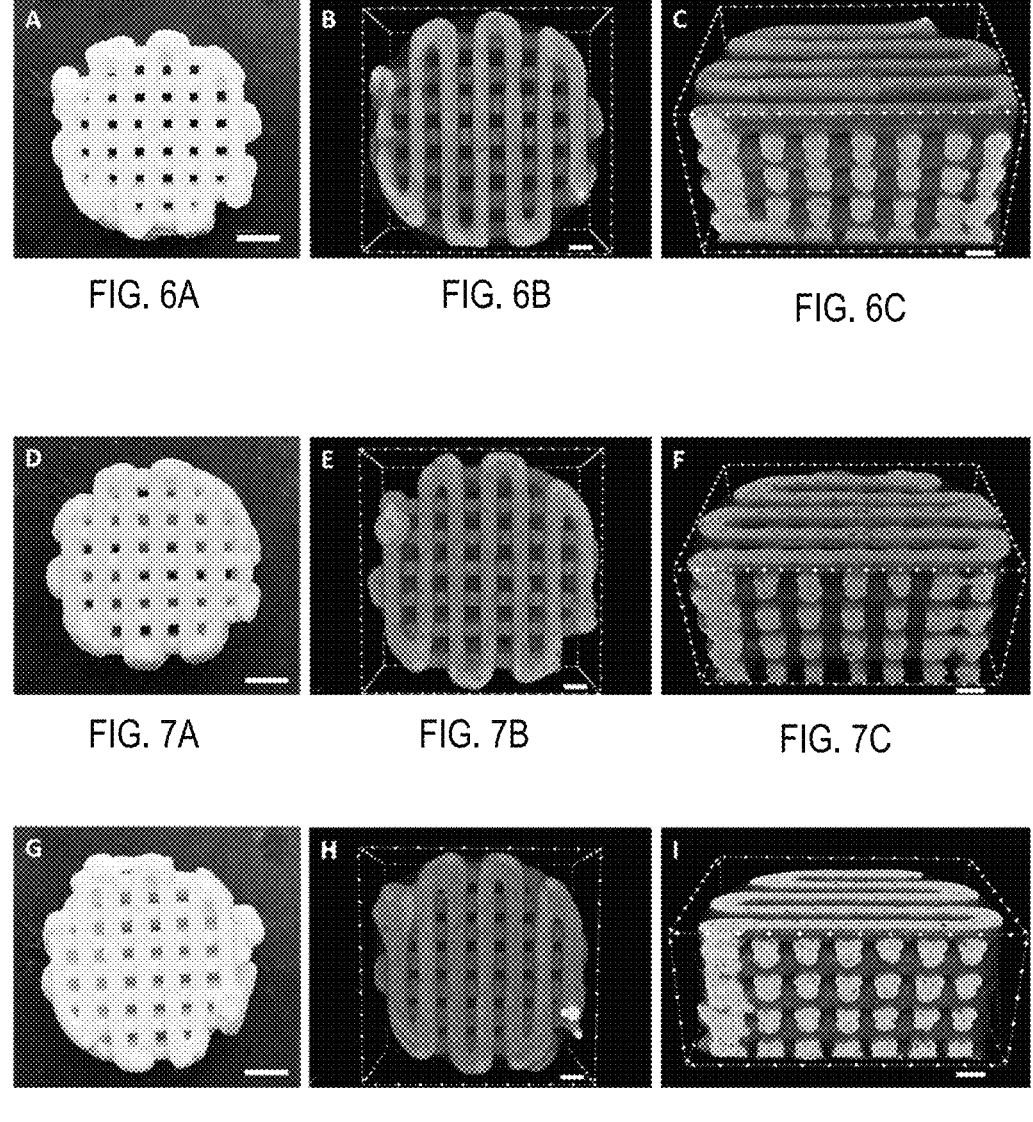
FIG. 6A is a top-down optical image of a hydroxyapatite ceramic scaffold in accordance with one or more embodiments of the present disclosure.
FIG. 6B is a top-down micro-CT image of a hydroxyapatite ceramic scaffold in accordance with one or more embodiments of the present disclosure.
FIG. 6C is a cross sectional micro-CT image of a hydroxyapatite ceramic scaffold in accordance with one or more embodiments of the present disclosure.
FIG. 7A is a top-down optical image of a beta-tricalcium phosphate ceramic scaffold in accordance with one or more embodiments of the present disclosure.
FIG. 7B is a top-down micro-CT image of a beta-tricalcium phosphate ceramic scaffold in accordance with one or more embodiments of the present disclosure.
FIG. 7C is a cross sectional micro-CT image of a beta-tricalcium phosphate ceramic scaffold in accordance with one or more embodiments of the present disclosure.
FIG. 8A is a top-down optical image of a hydroxyapatite/beta-tricalcium phosphate ceramic scaffold in accordance with one or more embodiments of the present disclosure.
FIG. 8B is a top-down micro-CT image of a hydroxyapa-tite/beta-tricalcium phosphate ceramic scaffold in accordance with one or more embodiments of the present disclosure.
FIG. 8C is a cross sectional micro-CT image of a hydroxy apatite/beta-tricalcium phosphate ceramic scaffold in accordance with one or more embodiments of the present disclosure.

FIG. 6A is a photograph of a printed HA scaffold. FIGS. 6B and 6C are microCT images of a printed HA scaffold. FIG. 7A is a photograph of a printed $-TCP scaffold. FIGS. 7B and 7C are microCT images of a printed β-TCP scaffold. FIG. 8A is a photograph of a printed HA/β-TCP scaffold. FIGS. 8B and SC are microCT images of a printed HA/β-TCP scaffold. The images demonstrate the reproducibility of the printing of scaffolds composed of 16 layers. The microCT analysis also showed the horizontal porosity achieved by changing the orientation of the fibers by 900 at every second layer. Scale bar=2 mm for the photographs and 1 mm for the microCT images.

Example 9: Ceramic Scaffold Sintering

After printing, the scaffolds were sintered in a furnace at 1200° C. for 6 h. The sintering program consisted of an initial heating to 400° C. to remove the organic components, performed at a slow rate of 1° C. increase/min to prevent the formation of cracks 30. Then, the samples were heated at 2° C. increase/min up to 1200° C., followed by a dwell time of 6 h. Finally, scaffolds were allowed to cool to room temperature.

Example 10: Physical Characterization of Ceramic Scaffolds

The structure and morphology of the scaffolds before and after the sintering process were assessed by SEM and microCT. For SEM, samples were sputter-coated with gold and imaged at different magnifications using a Quanta 400 ESEM FEG SEM (FEI Hillsboro, OR). MicroCT analysis was carried out using a SkyScan 1272 X-ray MicroCT (Bruker, Kontich, Belgium) with a pixel resolution of 7 μm and a Cu 0.1+ filter. Images were reconstructed using NRecon software, and 3D renderings were obtained using CTVox software. Analysis of scaffold shrinkage was carried out by comparing the diameter and height of the unsintered and sintered scaffolds with DataViewer software. Porosity was determined by employing CTAn analysis software to quantify the volume within the region of interest that was not occupied by radiopaque material (void volume), using a threshold of 21.5 μm which excluded the micropores from consideration. Pore interconnectivity was assessed by measuring the fraction of void volume accessible from outside of the scaffold through interconnections of at least 21.5 μm diameter between void volumes in adjacent voxels 32.

The high magnification SEM micrographs showed the different morphologies of the ceramic particles after the sintering process. FIGS. 9A and 9B are SEM micrographs of a sintered HA ceramic scaffold. FIGS. 10A and 10B are SEM micrographs of a sintered β-TCP ceramic scaffold. FIGS. 11A and 11B are SEM micrographs of a sintered hydroxyapatite/beta-tricalcium phosphate ceramic scaffold. HA scaffolds presented a structure with well-sintered particles and homogeneous microporosity, β-TCP scaffolds showed particles interconnected by necks suggesting a partial melting of the ceramic during the sintering process. The analysis of the surface of TCP/HA scaffolds confirmed the presence of two particle populations corresponding to the sintered HA and, similarly to the β-TCP scaffolds, the partial melting of the 0-TCP particles during the sintering process was also revealed. The SEM images also revealed the presence of microporosity in the structure of the scaffolds, with open micropores in the 5-10 μm range. The open micropores were evenly distributed throughout the structure regardless of scaffold composition.

Figures 12A, 12B, 12C:
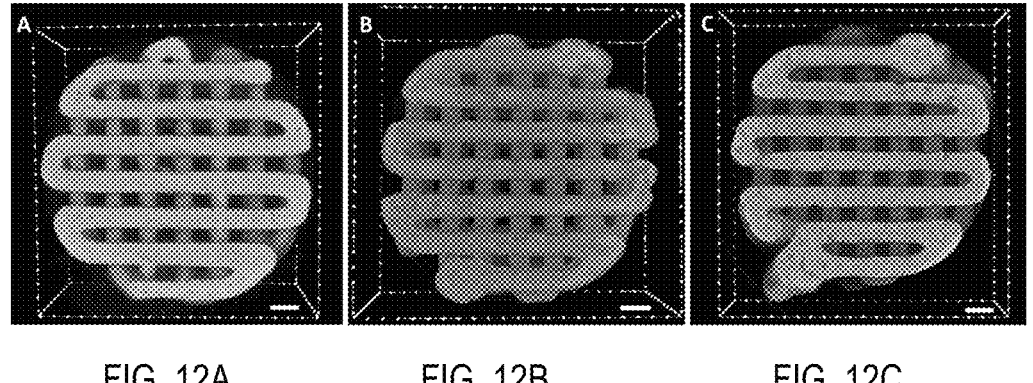
FIG. 12A is a top-down micro-CT image of a sintered hydroxyapatite ceramic scaffold in accordance with one or more embodiments of the present disclosure.
FIG. 12B is a top-down micro-CT image of a sintered beta-tricalcium phosphate ceramic scaffold in accordance with one or more embodiments of the present disclosure.
FIG. 12C is a top-down micro-CT image of a sintered hydroxyapatite/beta-tricalcium phosphate ceramic scaffold in accordance with one or more embodiments of the present disclosure.

The microscopic analysis of the ceramic scaffolds after the sintering process at 1200° C. was used to characterize the superficial morphology of the constructs (FIGS. 12A-12C). The micrographs showed the uniform horizontal pore size and fiber width in all printed scaffolds, with horizontal macropores of approximately 800 μm size, in accordance with the designed macropore structure.

The mass change of the binder during the burnout process was determined by thermogravimetric analysis (TGA) (TGA Q50; TA Instruments, New Castle, DE). Briefly, a 20 mg sample crosslinked under the same conditions as in the printing methodology was heated from 22° C. to 120° C. at a rate of 10° C./min, equilibrated at 120° C. for 20 min, and heated to 600° C. at 10° C./min. The TGA furnace was purged with argon (75 mL/min) during the heating process and with air during the cooldown.

Figure 13:
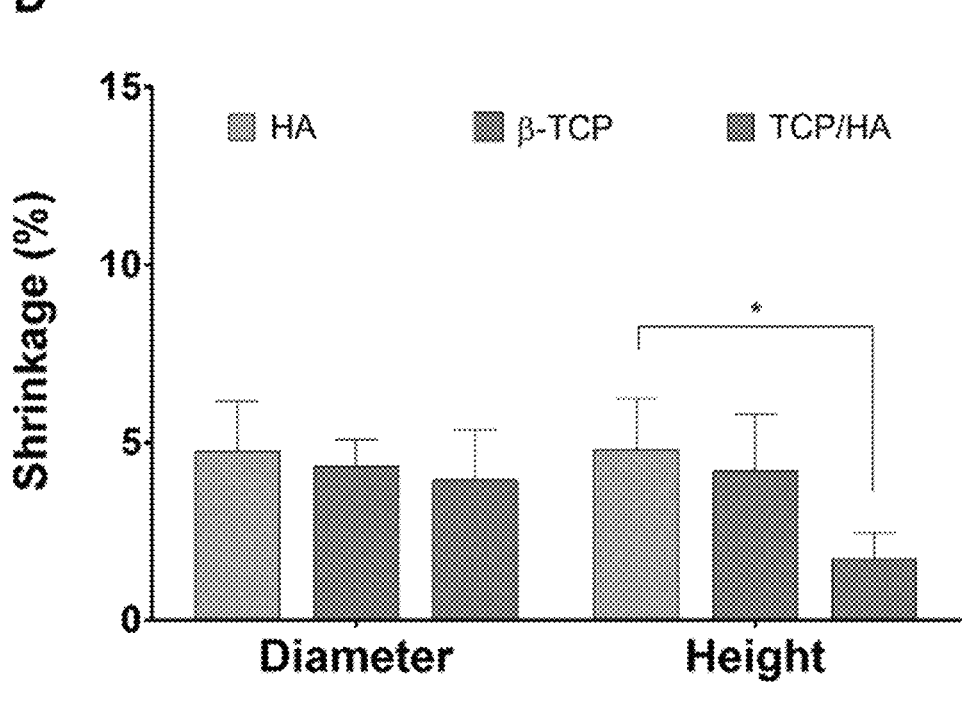
FIG. 13 is a chart showing shrinkage percentage after sintering for various scaffolds in accordance with one or more embodiments of the present disclosure.

The overall volumes, fiber widths, and pore sizes of the HA, β-TCP, and TCP/HA scaffolds were measured before and after sintering using the microCT scans to evaluate the effect of the sintering process on the dimensions of the scaffolds. The resulting analysis showed that for all scaffolds, independent of composition, the constructs possessed a similar structure, including fiber width and pore size. Furthermore, the dimensions of the scaffolds after sintering decreased by less than 5% for all compositions in both horizontal (4.8±1.3% for HA, 4.3±0.7% for β-TCP, and 4.0±1.4% for TCP/HA scaffolds) and vertical (4.8±1.4%, 4.2±1.6%, and 1.7±0.7%, for HA, β-TCP and TCP/HA, respectively) axes, thus maintaining the structural parameters of the design with high fidelity, as shown in FIG. 13. Despite the limitations of scanning resolution, ceramic particles can be seen after sintering, probably due to the densification that occurred during the sintering process at high temperatures.

Example 11: Structural Characterization of Ceramic Scaffolds

The crystal structures of the unsintered ceramic powders and sintered ceramic scaffolds were determined by X-ray diffraction (XRD) with Cu Ka radiation (40 kV, 40 mA) and analyzed using a D/MAX Ultima II X-ray diffractometer (Rigaku Corp., Tokyo, Japan) operated at a step size of 0.020 over the 20 range of 20-50° at room temperature. Sintered ceramic scaffolds were ground to a fine powder using a mortar and pestle before the analysis. Rietveld refinement was used to calculate the detailed crystal structural information of the ceramic scaffolds after the sintering process, as described previously. The Rietveld method uses the crystal structure and diffraction peaks to generate an X-ray diffraction pattern via a process of least-squares refinement, which minimizes the differences between the observed and calculated patterns. Specifically, Rietveld refinement performed with HighScore Plus 3.0d (PANalytical, Almelo, The Netherlands) was applied in the present work. The background ("Chebyshev I" function), zero drift, absorption, lattice parameters, and atomic coordinates were refined, and the peak shape parameters were set as a modified pseudo-Voigt (PV) function. The initial models for the refinements were derived from Inorganic Crystal Structure Database (ICSD) reported structures (#923, #97500 and #171549 for α-TCP, β-TCP, and HA, respectively).

Figure 14:
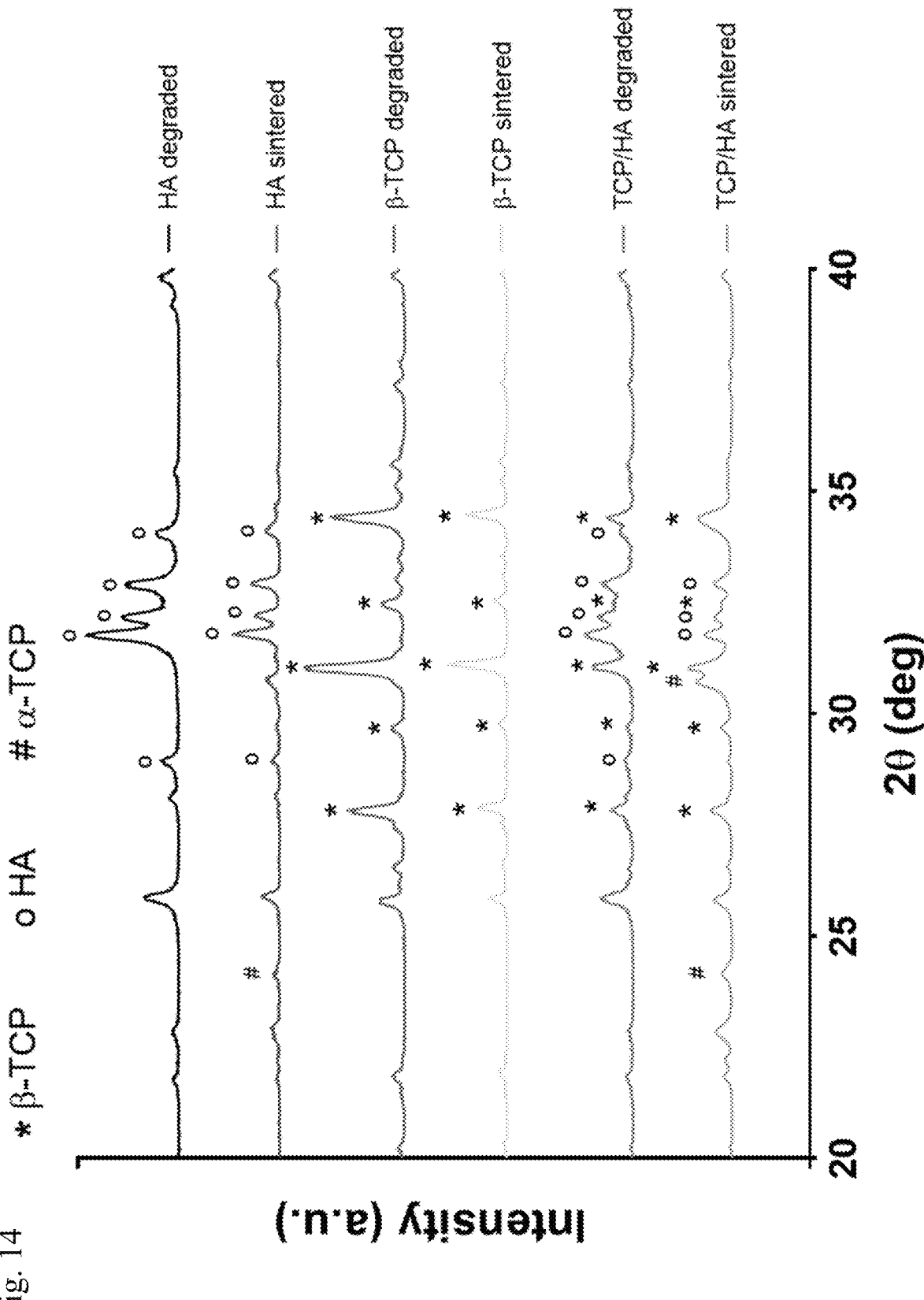
FIG. 14 is a plot showing x-ray diffractograms for various ceramic powders and sintered ceramic materials in accordance with one or more embodiments of the present disclosure.

FIG. 14 shows the XRD diffractogram of the raw powders and scaffolds sintered at 1200° C. The raw HA, β-TCP and TCP/HA mixture powders showed peak intensities matching the Inorganic Crystal Structural Database (ICSD) patterns for each component. Similarly, sintered β-TCP scaffolds showed peak intensities according to the powder diffraction pattern of the β-TCP ICSD card, suggesting that the sintering process did not alter the crystal structure of the scaffold composition. In contrast, the diffractogram of sintered HA scaffolds showed the presence of peak intensities corresponding to the composition of α-TCP. Indeed, the Rietveld refinement of the acquired diffractogram revealed the transformation of approximately 34% of the HA into α-TCP. Similarly, the TCP/HA sintered scaffolds showed the presence of α-TCP peaks in the powder diffraction pattern. The Rietveld refinement indicated that the phase composition of the TCP/HA samples included approximately 73% of β-TCP, 12% of α-TCP, and 15% of HA.

Figure 15:
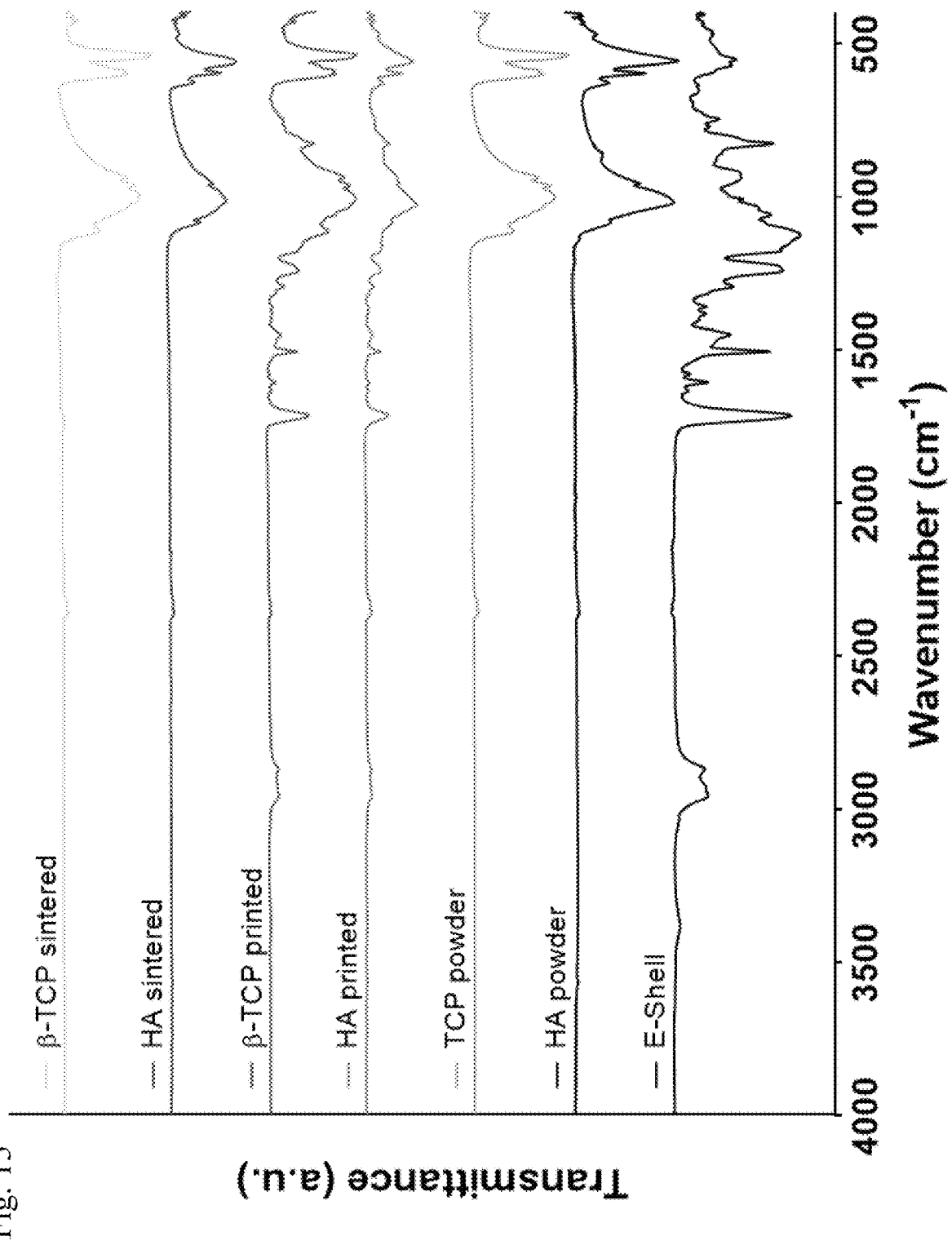
FIG. 15 is a plot showing FTIR spectra for various ceramic materials before and after sintering accordance with one or more embodiments of the present disclosure.

The functional groups present in the chemical structures of the raw materials (E-Shell®300, HA, and β-TCP) and the scaffolds before and after sintering at 1200° C. were determined by Fourier-transform infrared spectroscopy (FTIR) (Nicolette IS50, Thermo Fisher Sci., Waltham, MA) over a wavenumber range of 400-4000 cm-1 and with a resolution of 0.5 cm$^1$ (FIG. 15).

Example 12: Mechanical Characterization

Scaffolds (n=5; 10 mm in diameter, 5 mm height) were tested using a compressive mechanical testing apparatus (858 MiniBionixII®, MTS, Eden Prairie, MN; 10 kN load cell) and evaluated using the TestStar 790.90 mechanical data analysis package included in the manufacturer's software. Uniaxial compression testing was carried out following the guidelines of the American Society for Testing and Materials, specifically ASTM D695-15 was adapted to bone tissue scaffolds and used for compression testing. The height-to-diameter aspect ratio of the scaffolds was maintained at 1:2, in order to facilitate uniaxial load application and avoid buckling events34. The test analyzed the compressive strength and modulus through compression applied perpendicularly to the printing plane with a crosshead speed of 2 mm/min after an initial pre-load of 25 N Stress-strain curves were calculated from the load vs. displacement data using the initial dimensions of the sample. The compressive moduli of the HA (28.0±13.8 MPa) and TCP/HA (25.1±14.0 MPa) scaffolds, and β-TCP scaffolds (44.9±19.4 MPa) were statistically similar.

Example 13: Dissolution

The sintered scaffolds (n=3 per time point) were immersed in 5 ml of PBS (pH 7.4) and incubated at 37° C. in an orbital shaker at 110 rpm. Every two days, the dissolution buffer solution was removed, its pH level was measured using an Accumet pH/ORP Meter (Fischer Scientific, Waltham, MA), and fresh PBS was added to replace the buffer solution. At 3, 7, 14, 21, and 28 days, scaffolds were removed from PBS, washed with distilled water, and vacuum-dried for 48 h. Dissolution was then calculated as shown in Eq. 1:

$$\text{Mass loss (\%)} = \frac{M_i - M_f}{M_t} \cdot 100 \qquad \text{Eq. (1)}$$

where $M_i$ and $M_f$ represent the initial mass and final mass at each time point, respectively.

MicroCT and XRD analyses as described above were also performed in order to investigate the structural and compositional changes of the scaffolds after the 28-day incubation period, respectively.

Figure 17:
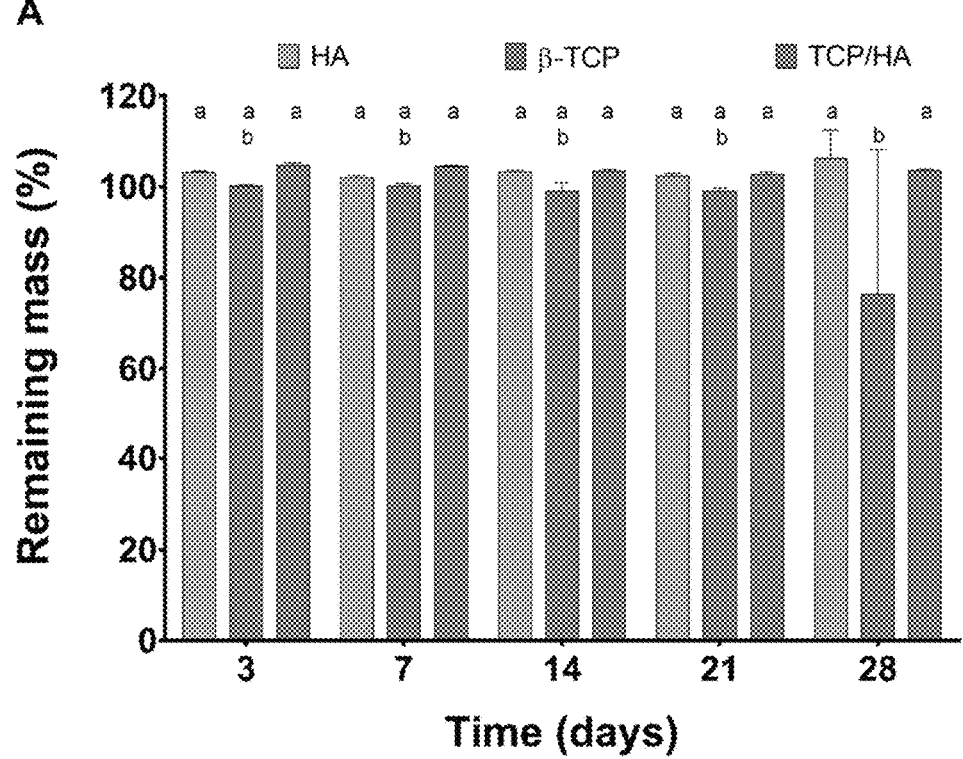
FIG. 17 is a plot showing remaining mass of various scaffold materials after varying amounts of time in a PBS buffer in accordance with one or more embodiments of the present disclosure.

At this last time point, β-TCP scaffolds lost their structural integrity and were fragmented in multiple pieces, whose masses were summed for this final measurement, and the dissolution study was discontinued upon this observation. The mass loss over time is shown in FIG. 17. The scaffold mass was not found to be significantly different after incubation in the PBS solution for 28 days, for which ji-TCP scaffold mass differed from the other two compositions ($p<0.05$) but was similar to previous β-TCP timepoints ($p>0.05$). The pH values of the dissolution buffer solution were also monitored throughout the dissolution course. The pH of the buffer solution for HA and TCP/HA scaffolds decreased during the first days of incubation from 7.4 to 6.90±0.03 and 6.99±0.02, respectively. In contrast, the pH of the incubation medium for β-TCP scaffolds increased to 7.59±0.02 after scaffold immersion. However, within 21 days, all compositions stabilized at pH 7.36±0.02 and no statistical differences were found for the remainder of the study ($p>0.05$).

The structure of the scaffolds after 28 days of incubation in PBS was evaluated using microCT. These results showed that the HA and TCP/HA scaffolds maintained a homogeneous macroscopic structure similar to that of the scaffolds before incubation. However, the 28-day incubation substantially affected the structural integrity of β-TCP scaffolds, and microCT scanning was performed on the largest recoverable fragment remaining within the dissolution buffer. Although no appreciable mass loss was measured, a breakdown in the structure was evident. Microscopic alterations in the structure of the scaffolds were found in the microCT analysis. The presence of structural defects parallel to the axis of the fibers was identified in the HA scaffolds. However, these changes were found throughout the structure of the β-TCP scaffolds.

Example 14: Ink-Storability

The printing properties of the composite ceramic inks were monitored for 14 days. Briefly, inks were prepared as explained in Section 2.2 and placed in printing syringes. The ink-filled syringes were placed in the printing heads and scaffolds (3 replicates per ink, 8 layers high) were printed using the same printing parameters as in Section 2.2. The pore size, fiber width, and porosity of the printed scaffolds were evaluated by microCT in order to analyze the effect of ink storage on the overall structure of the constructs.

Figure 16:
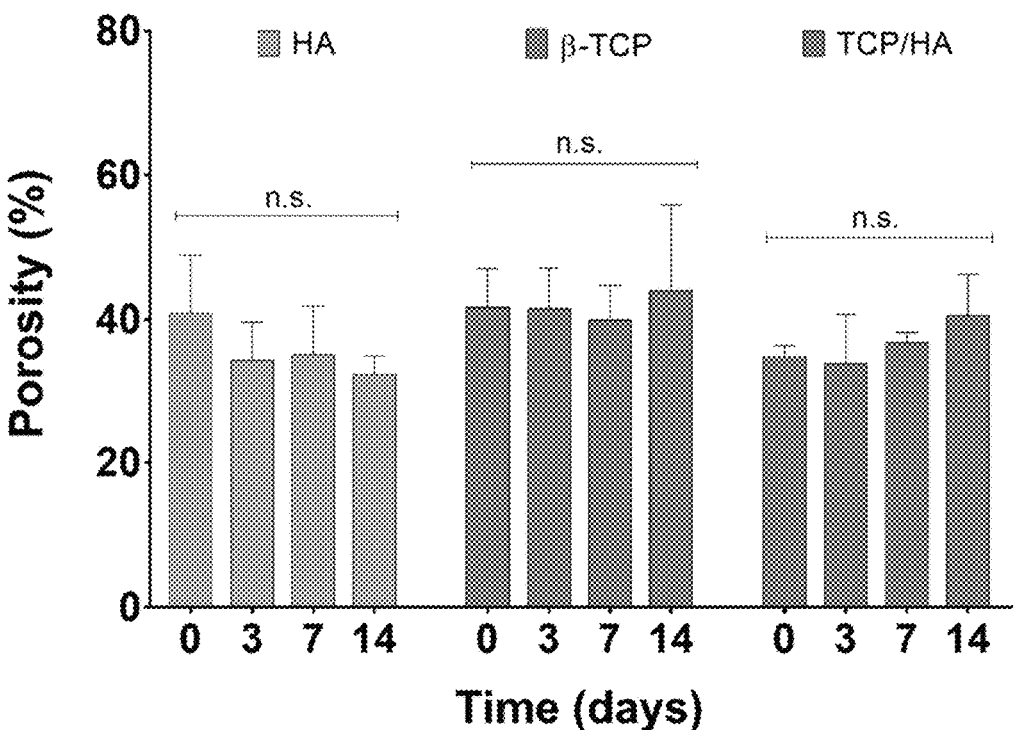
FIG. 16 is a plot showing porosity of various scaffolds prepared from inks having been aged for different amounts of time in accordance with one or more embodiments of the present disclosure.

The printing parameters set for the printing of scaffolds immediately after preparing the inks were still suitable to obtain scaffolds with similar structures after 14 days of ink storage. MicroCT reconstructions of the scaffolds printed at 0, 3, 7 and 14 days after ink preparation revealed that, using the same printing parameters, the structure and pattern of the obtained scaffolds was not significantly altered. Porosity measurements of the scaffolds, as shown in FIG. 16, revealed that printing of the inks using the same printing conditions throughout the 14-day period led to scaffolds with similar porosities (p>0.05), as shown in the microCT analysis.

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112(f) for any limitations of any of the claims herein, except for those in which the claim expressly uses the words 'means for' together with an associated function.

What is claimed as new and desired to be protected by Letters Patent of the United States is:

1. A method of making a biocompatible article comprising:
   preparing a 3D-printable mixture, wherein the preparing comprises conjugating an alkyne-terminated polymer to a peptide to form a peptide-containing composite, and wherein the peptide is a tissue-specific bioactive peptide selected from the group consisting of an osteogenic bone morphogenetic protein mimetic peptide comprising a peptide having the sequence of SEQ ID NO:1, an osteogenic glycine-histidine-lysine peptide comprising a peptide having the sequence of SEQ ID NO:2 or SEQ ID NO:4, a chondrogenic N-cadherin peptide comprising a peptide having the sequence of SEQ ID NO:3 or SEQ ID NO;5, and combinations thereof; and
   depositing successive layers of the mixture in a predetermined pattern to form a porous biocompatible article, wherein the predetermined pattern comprises a porosity suitable for a bone or cartilage scaffold.

2. The method of claim 1, wherein the conjugating comprises mixing the alkyne-terminated polymer, the peptide and a catalyst in an aqueous medium at a temperature of from 20 to 70° C. for a time of from 12 to 48 hours.

3. The method of claim 1, wherein the alkyne-terminated polymer is alkyne-terminated poly(ε-caprolactone).

4. The method of claim 1, wherein the alkyne-terminated polymer has a molecular weight of from 4 to 50 kDa.

5. The method of claim 1, wherein the catalyst is chloro(pentamethylcyclopentadienyl)(cycloocta-diene)ruthenium (II).

6. The method of claim 1, wherein the depositing comprises extruding the peptide-containing composite at a temperature of from 70 to 100° C.

7. The method of claim 1, further comprising cell seeding of the biocompatible article.

8. The method of claim 1, wherein the porosity is from 60 to 85%.

9. The method of claim 1, wherein the biocompatible article comprises an average pore size of from 300 to 600 μm.

10. The method of claim 1, wherein the 3D printable mixture comprises a ceramic material and a binder, and wherein the 3D printable mixture comprises from 50 wt. % to 80 wt. % of the ceramic material.

11. The method of claim 10, wherein the ceramic material is selected from the group consisting of hydroxyapatite, alpha-tricalcium phosphate, beta-tricalcium phosphate, and combinations thereof.

12. The method of claim 10, wherein the ceramic material is a powder.

13. The method of claim 12 wherein the powder has an average particle size of from 50 nm to 50 μm.

14. The method of claim 10, wherein the binder comprises tetrahydrofurfuryl methacrylate, urethane dimethacrylate, diphenyl(2,4,6-trimethylbenzoyl)phosphine oxide, and combinations thereof.

15. The method of claim 10, wherein the depositing comprises:
    extruding the mixture at a temperature of from 10 to 40° C. and a pressure of from 0.3 to 5 bar to form a layer;
    applying ultraviolet radiation to the layer; and
    repeating the extruding and applying steps until a desired number of layers is achieved.

16. The method of claim 10 further comprising:
    sintering the article at a temperature of from 1000 to 1400° C. for 3 to 12 hours to form a sintered article.

17. The method of claim 15 further comprising rotating the article by about 90 degrees after a predetermined number of depositing steps.

18. The method of claim 10, wherein the porosity is from 20 to 55%.

19. The method of claim 10, wherein the biocompatible article comprises an average pore size of from 600 to 1000 μm.

20. The method of claim 1, wherein the peptide is a tissue-specific bioactive peptide, the depositing comprises 3D-printing the successive layers of the 3D-printable mixture and the porous biocompatible article comprises a tissue-specific bioactivity suitable for a bone or cartilage scaffold.

21. The method of claim 20, wherein the alkyne-terminated polymer is an alkyne-terminated poly(ε-caprolactone).

22. An article formed from the method of claim 1.

23. The article of claim 22, wherein the article is selected from the group consisting of a vascularized graft, a tendon implant and a ligament implant.

24. A biocompatible 3D printable ink composition comprising:

a biocompatible ceramic material;

a peptide-containing composite comprising a polymer and
a peptide conjugated to the polymer; and a binder;

wherein the peptide is a tissue-specific bioactive peptide
selected from the group consisting of an osteogenic
bone morphogenetic protein mimetic peptide comprising a peptide having the sequence of SEQ ID NO:1, an
osteogenic glycine-histidine-lysine peptide comprising
a peptide having the sequence of SEQ ID NO:2 or SEQ
ID NO:4, a chondrogenic N-cadherin peptide comprising a peptide having the sequence of SEQ ID NO:3 or
SEQ ID NO;5, and combinations thereof;

wherein the composition comprises from 50 wt. % to 80
wt. % of the ceramic material; and wherein the ceramic material is selected from the group
consisting of hydroxyapatite, alpha-tricalcium phosphate, beta-tricalcium phosphate, and combinations
thereof.

25. The composition of claim 24, wherein the ceramic
material is a powder.

26. The composition of claim 24, wherein the powder has
an average particle size of from 50 nm to 50 μm.

27. The composition of claim 24, wherein the binder
comprises tetrahydrofurfuryl methacrylate, urethane dimethacrylate, diphenyl(2,4,6-trimethylbenzoyl)phosphine
oxide, and combinations thereof.

* * * * *

SEQUENCE LISTING

```
<160> NUMBER OF SEQ ID NOS: 5

<210> SEQ ID NO 1
<211> LENGTH: 12
<212> TYPE: PRT
<213> ORGANISM: Artificial Sequence
<220> FEATURE:
<223> OTHER INFORMATION: Osteoogenic bone morphogenetic protein mimetic
      peptide

<400> SEQUENCE: 1

Gly Gly Gly Arg His Val Arg Ile Ser Arg Ser Leu
1               5                   10

<210> SEQ ID NO 2
<211> LENGTH: 8
<212> TYPE: PRT
<213> ORGANISM: Artificial Sequence
<220> FEATURE:
<223> OTHER INFORMATION: Osteogenic glycine-histidine-lysine peptide

<400> SEQUENCE: 2

Gly Gly Gly Gly His Lys Ser Pro
1               5

<210> SEQ ID NO 3
<211> LENGTH: 8
<212> TYPE: PRT
<213> ORGANISM: Artificial Sequence
<220> FEATURE:
<223> OTHER INFORMATION: Chondrogenic N-cadherin peptide

<400> SEQUENCE: 3

Gly Gly Gly His Ala Val Asp Ile
1               5

<210> SEQ ID NO 4
<211> LENGTH: 13
<212> TYPE: PRT
<213> ORGANISM: Artificial Sequence
```

-continued

```
<220> FEATURE:
<223> OTHER INFORMATION: Osteoogenic bone morphogenetic protein mimetic
      peptide with additional lysine

<400> SEQUENCE: 4

Gly Gly Gly Arg His Val Arg Ile Ser Arg Ser Leu Lys
1               5                   10

<210> SEQ ID NO 5
<211> LENGTH: 9
<212> TYPE: PRT
<213> ORGANISM: Artificial Sequence
<220> FEATURE:
<223> OTHER INFORMATION: Chondrogenic N-cadherin peptide with additional
      lysine

<400> SEQUENCE: 5

Gly Gly Gly His Ala Val Asp Ile Lys
1               5
```